(12) United States Patent
Naganawa et al.

(10) Patent No.: US 8,809,524 B2
(45) Date of Patent: Aug. 19, 2014

(54) PHENYLACETIC ACID COMPOUND

(71) Applicant: Ono Pharmaceutical Co., Ltd., Osaka (JP)

(72) Inventors: Atsushi Naganawa, Osaka (JP); Toshihiko Nagase, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/854,329

(22) Filed: Apr. 1, 2013

(65) Prior Publication Data

US 2013/0225808 A1   Aug. 29, 2013

Related U.S. Application Data

(62) Division of application No. 13/627,720, filed on Sep. 26, 2012, now Pat. No. 8,476,266, which is a division of application No. 12/672,762, filed as application No. PCT/JP2008/064429 on Aug. 11, 2008, now Pat. No. 8,318,729.

(30) Foreign Application Priority Data

Aug. 10, 2007   (JP) ................................. 2007-208815

(51) Int. Cl.
  *C07D 265/36*   (2006.01)
  *A61K 31/00*    (2006.01)
  *C07C 57/32*    (2006.01)

(52) U.S. Cl.
  USPC ...................................... 544/105; 514/230.5

(58) Field of Classification Search
  USPC ........................................................ 544/105
  See application file for complete search history.

(56) References Cited

U.S. PATENT DOCUMENTS

| | | | |
|---|---|---|---|
| 5,116,853 | A | 5/1992 | Mase et al. |
| 6,083,974 | A | 7/2000 | Honma et al. |
| 2003/0176400 | A1 | 9/2003 | Torisu et al. |

FOREIGN PATENT DOCUMENTS

| | | |
|---|---|---|
| EP | 0 869 949 | 10/1998 |
| WO | WO 03078409 | 9/2003 |
| WO | WO 2005028455 | 3/2005 |
| WO | WO 2009022687 | 2/2009 |

OTHER PUBLICATIONS

Decision of Grant for Russian Patent Application No. 2010108470 dated Aug. 11, 2012.
Banker, G., et al. "Modern Pharmaceuticals." 3ed., 1996, 451 & 596.
Copending U.S. Appl. No. 10/544,646, filed Nov. 23, 2005.
Ono Pharmaceutical Co., Ltd. "Office Action." Australian Patent Application No. 2004274324. Applicant: Ono Pharmaceutical Co. Ltd. Mailed: May 18, 2009.
Ono Pharmaceutical Co., Ltd. "Office Action." New Zealand Patent Application No. 545934. Applicant: Ono Pharmaceutical Co., Ltd. Mailed: May 21, 2008.
Ono Pharmaceutical Co., Ltd. "Office Action." Russian Patent Application No. 2006112573. Applicant: Ono Pharmaceutical Co., Ltd. Mailed: Sep. 16, 2004.
Ono Pharmaceutical Co., Ltd. "Office Action." U.S. Appl. No. 10/572,578. Applicant: Atsushi Naganawa. Mailed: May 23, 2007.
West, Anthony. "Solid state of chemistry and its applications." 1988, 358 & 365.
Wolff, Manfred. "Burger's Medicinal Chemistry and Drug Discovery." 5th ed., part 1. 1995, 975-977.
Vippagunta et al. "Crystalline Solids" Advanced Drug Delivery Reviews, vol. 48, pp. 3-26 (2001).
Gavezzotti "Are Crystal Structures Predictable?" Accounts of Chemical Research, vol. 27, pp. 309-314 (1994).
Wolff Manfred E. "Burger's Medicinal Chemistry, 5ed, Part 1" John Wiley & Sons, 1995, pp. 975-977.
Banker, G.S. et al. "Modern Pharmaceutices, 3ed." Marcel Dekker, New York, 1996, pp. 451 and 596.
Cecil Textbook of Medicine, 20th Edition, vol. 2, 1996, pp. 1739-1747.

*Primary Examiner* — Kahsay Habte
(74) *Attorney, Agent, or Firm* — Millen, White, Zelano & Branigan, P.C.

(57) ABSTRACT

A compound represented by formula (I), wherein
$R^1$ represents a hydrogen atom, etc.,
$R^2$ and $R^3$ each independently represents a hydrogen atom, optionally oxidized C1-4 alkyl group or optionally protected hydroxyl group, or $R^2$ and $R^3$ taken together represent optionally oxidized C2-5 alkylene group,
$R^4$ represents an optionally oxidized C1-6 alkyl group, etc.,
$R^5$ represents an optionally oxidized C1-6 alkyl group, etc.,
$R^6$ represents an optionally oxidized C1-6 alkyl group, etc.,
m represents 0 or an integer from 1 to 3,
n represents 0 or an integer from 1 to 4, and
i represents 0 or an integer from 1 to 7.

8 Claims, No Drawings

PHENYLACETIC ACID COMPOUND

TECHNICAL FIELD

The present invention relates to a novel phenylacetic acid compound or a salt thereof, and a medicament comprising the same as an active ingredient. In more detail, the present invention relates to a novel phenylacetic acid compound represented by formula (I)

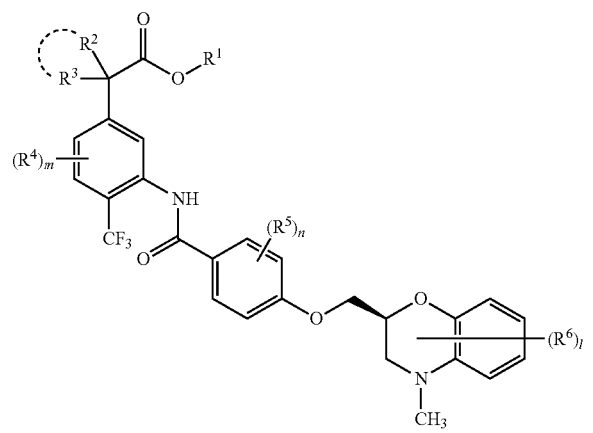

(I)

wherein all symbols in the formula have the same meanings described below, a salt thereof, an N-oxide thereof or a solvate thereof, or a prodrug thereof, and a medicament comprising the same as an active ingredient.

BACKGROUND ART

Prostaglandin $D_2$ (abbreviated as $PGD_2$) is known as a metabolite produced via an arachidonic acid cascade and is considered to be one of the chemical mediators involved in allergic diseases such as allergic rhinitis, bronchial asthma and allergic conjunctivitis. It is known that $PGD_2$ is mainly produced in and released from mast cells and that the released $PGD_2$ provides contraction of bronchus, promotion of vascular permeability, dilation or contraction of blood vessels, promotion of mucus secretion, inhibition of platelet aggregation, etc. It has been also reported that $PGD_2$ induces bronchoconstriction and nasal obstruction in vivo and increased the production of $PGD_2$ in pathological lesion of patients suffering from systemic mastocytosis, allergic rhinitis, bronchial asthma, atopic dermatitis, urticaria, etc. (N. Engl. J. Med. 1980; 303: 1400-4, Am. Rev. Respir. Dis. 1983; 128: 597-602, J. Allergy Clin. Immunol. 1991; 88: 33-42, Arch. Otolaryngol. Head Neck Surg. 1987; 113: 179-83, J. Allergy Clin. Immunol. 1988; 82: 869-77, J. Immunol. 1991; 146: 671-6, J. Allergy Clin. Immunol. 1989; 83; 905-12, N. Eng. J. Med. 1986; 315; 800-4, Am. Rev. Respir. Dis. 1990; 142, 126-32, J. Allergy Clin. Immunol. 1991; 87: 540-8, J. Allergy Clin. Immunol 1986; 78: 458-61). $PGD_2$ has been also reported to be involved in neural activity, particularly in sleeping, hormone secretion, and pain. Furthermore, it has been also reported that it is involved in platelet aggregation, glycogen metabolism and adjustment of intraocular pressure, etc.

WO 2005/028455 (Patent Document 1, hereinafter) describes that a compound represented by formula (A) binds to a DP receptor and behaves as an antagonist:

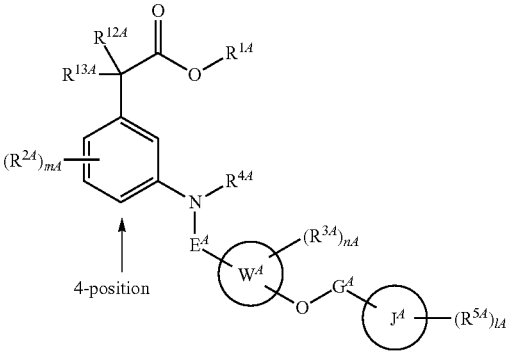

(A)

wherein,
$R^{1A}$ represents (1) a hydrogen atom, (2) C1-4 alkyl group, etc.,
$E^A$ represents —CO group etc.,
$R^{2A}$ represents (1) a halogen atom, (2) C1-6 alkyl group, (3) C1-6 alkoxy group, (4) hydroxyl group, (5) trihalomethyl group, (6) cyano group, (7) phenyl group, (8) pyridyl group, (9) nitro group, (10) —$NR^{6A}R^{7A}$ group, (11) C1-4 alkyl group substituted with —$OR^{b\,8A}$ group, (12) oxidized C1-6 alkyl group, (13) —$SO_2R^{11A}$ group, (14) —$SOR^{11A}$ group, or (15) —$SR^{11A}$ group,
$R^{3A}$ represents (1) a halogen atom or (2) C1-6 alkyl group, etc.,
$R^{6A}$ and $R^{7A}$ each independently represents a hydrogen atom or C1-4 alkyl group,
$R^{8A}$ represents C1-4 alkyl, phenyl, or pyridyl group,
$R^{4A}$ represents (1) a hydrogen atom, etc.,
$R^{5A}$ represents (1) C1-6 alkyl, or (2) C1-10 alkoxy, etc.,
$R^{11A}$ represents C1-6 alkyl group, or optionally substituted phenyl group,
ring $W^A$ represents a C5-12 monocyclic or bicyclic carbon ring, etc.,
$G^A$ represents (1) C1-6 alkylene group etc. having 0-2 hetero atoms selected from the group consisting of a nitrogen atom, an oxygen atom and a sulfur atom,
ring $J^A$ represents a 5-12 membered monocyclic or bicyclic heterocyclic ring, etc.,
mA represents 0 or an integer from 1 to 4,
nA represents 0 or an integer from 1 to 4,
iA represents 0 or an integer from 1 to 11,
$R^{12A}$ and $R^{13A}$ each independently represents (1) optionally oxidized C1-4 alkyl group, (2) a halogen atom, (3) trihalomethyl group, (4) optionally protected hydroxyl group, (5) optionally protected amino group, (6) optionally substituted phenyl group, (7) optionally substituted pyridyl group, or (8) a hydrogen atom, or $R^{12A}$ and $R^{13A}$ taken together represent (1) oxo group, (2) C2-5 alkylene group in which a carbon atom is optionally replaced by an oxygen atom, nitrogen atom, or sulfur atom, wherein the C2-5 alkylene group is optionally substituted by a substituent, or (3) optionally substituted C1-6 alkylidene group.
(The necessary parts of the explanation for the groups are selectively described.)
(See Patent Document 1).

WO 03/078409 (Patent Document 2, hereinafter) describes that a compound represented by formula (B) binds to a DP receptor and behaves as an antagonist:

(B)

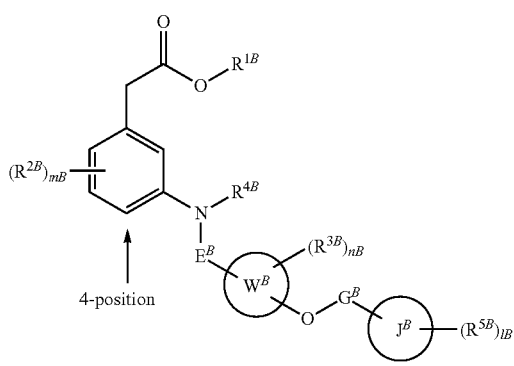

wherein
$R^{1B}$ represents (1) a hydrogen atom or (2) C1-4 alkyl group, etc.,
$E^B$ represents —C(=O)— group, etc.,
$R^{2B}$ represents (1) a halogen atom, (2) C1-6 alkyl group, (3) C1-6 alkoxy group, (4) hydroxyl group, (5) trihalomethyl group, (6) cyano group, (7) phenyl group, (8) pyridyl group, (9) nitro group, (10) —$NR^{6B}R^{7B}$ group, or (11) C1-4 alkyl group substituted by —$OR^{6B}$ group,
$R^{3B}$ represents (1) a halogen atom or (2) C1-6 alkyl group, etc.,
$R^{6B}$ and $R^{7B}$ each independently represents a hydrogen atom or C1-4 alkyl group,
$R^{8B}$ represents C1-4 alkyl group, phenyl group, or pyridyl group,
$R^{4B}$ represents (1) hydrogen atom, etc.,
$R^{5B}$ represents (1) C1-6 alkyl group, or (2) C1-10 alkoxy group, etc.,
ring $W^B$ represents C5-12 monocyclic or bicyclic carbon ring, etc.,
$G^B$ represents (1) C1-6 alkylene group, etc. containing 0-2 hetero atoms selected from the group consisting of a nitrogen atom, an oxygen atom and a sulfur atom,
ring $J^B$ represents 5-12 membered monocyclic or bicyclic heterocyclic ring, etc.,
mB represents 0 or an integer from 1 to 4,
nB represents 0 or an integer from 1 to 4,
iB represents 0 or an integer from 1 to 11.
(The necessary parts of explanation for the groups are selectively described.)
(See to Patent Document 2).

Although Patent Document 1 and 2 list the types of substituents represented by $R^{2A}$ and $R^{2B}$, there is no description of the most preferable substitution position, and there is no description or suggestion of the effects due to the substituent type and the substitution position.

Further, there is no description in Patent Documents 1 and 2 that the drug-metabolizing enzyme is inhibited by introducing a specific substituent at a specific substitution position of the compound represented by formulae (A) and (B), and therefore naturally, no description or suggestion for the means to solve the problem is given therein.

Additionally, there is no description in Patent Documents 1 and 2 that, depending on the combination of the substituent type and the substitution position, the compounds represented by formulae (A) and (B) may have insufficient selectivity against other receptors and therefore naturally, no description or suggestion for the means to solve the problem is given therein.

DISCLOSURE OF INVENTION

There is a need for a safe DP receptor antagonist compound, which has significant antagonistic activity, does not inhibit a drug-metabolizing enzyme, and has good receptor selectivity.

That is, if the compound inhibits any drug-metabolizing enzyme, there is a possibility that drug interaction with a companion drug which may cause serious side-effects may occur, and this becomes a major problem for use of the compound as a medicinal drug.

An arachidonic acid cascade includes various types of prostaglandins, and there are many prostaglandin receptors, including subtypes thereof, which correspond to each compound, and which respectively relate to different pharmacological effects. Therefore, to produce a new safe medicinal drug having reduced side-effects, it is also important for the drug to have sufficient selectivity against other prostaglandin receptors.

For example, an $EP_1$ receptor, $EP_2$ receptor, $EP_3$ receptor, and $EP_4$ receptor are known as an EP receptor subtype whose ligand is prostaglandin E.

Since the $EP_2$ receptor agonist has vascular smooth muscle relaxant activity, there is concern that in causes reduction in blood pressure as a systemic effect. If the $EP_2$ receptor agonist relaxes local vascular smooth muscle surrounding the nose, oedema of the nasal mucosa may occur associated to the reduction of the vascular resistance, whereby the remedial effect against the symptoms of allergic rhinitis (nasal obstruction, etc.) which is expected to be an effect of the DP receptor antagonist, will be adversely affected. Additionally, the uterine-relaxing action possessed by the $EP_2$ receptor agonists is regarded as a side effect in the point of view of the prevention and/or treatment of diseases which the DP receptor antagonist compounds are intended for.

That is, in the development of the DP receptor antagonist compounds, it is especially important that they have sufficient selectivity against the $EP_2$ receptor.

The inventors of the present invention found that introduction of a methyl group at 4-position of the phenylacetic acid moiety of a compound represented by formulae (A) and (B) improves the binding affinity against the DP receptors much more than non-substituted compounds. However, it became clear that the introduction of a methyl group also improves an inhibitory effect against CYP3A4 which is a drug-metabolizing enzyme.

The inventors of the present invention also found that introduction of a chloro group at 4-position of the phenylacetic acid moiety of the compound represented by formulae (A) and (B) improves the binding affinity to the DP receptors much more than the non-substituted compounds. However, it became clear that when a hydrogen atom or a chloro group is at 4-position of the phenylacetic acid moiety, the binding affinity to the $EP_2$ receptors is extremely high. Introduction of a chloro group does not affect CYP3A4, however, the strong bond with the $EP_2$ receptor is a significant problem.

The inventors of the present invention have made intensive investigations of many types of substituents and substitution positions to solve the above-mentioned problem and have unexpectedly discovered that a compound having the basic skeleton of the compound represented by formula (A) per se but having a trifluoromethyl group introduced at 4-position of the phenylacetic acid moiety, i.e., a compound represented by formula (I)

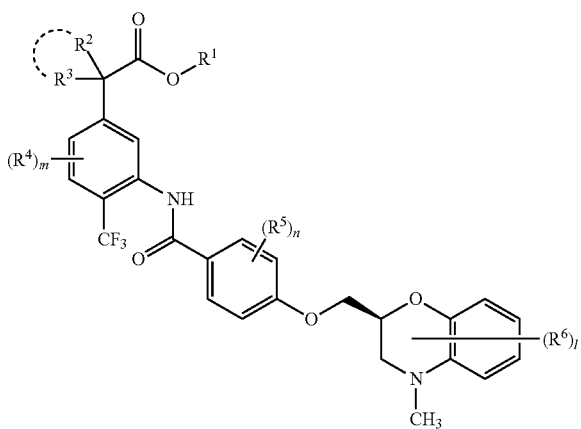

(I)

wherein all symbols in the formula, have the same meanings described below, does not strongly inhibit the drug-metabolizing enzyme, while maintaining or improving the significant DP receptor antagonistic activity. Additionally, they discovered that the compound has good receptor selectivity against DP receptor. Especially, it was found that the compound represented, by formula (I), wherein $R^2$ and $R^3$ taken together represent optionally oxidized C2-5 alkylene group, especially —$(CH_2)_2$—, has much higher selectivity to the DP receptors.

That is, the present invention relates to (1) a compound represented by formula (I)

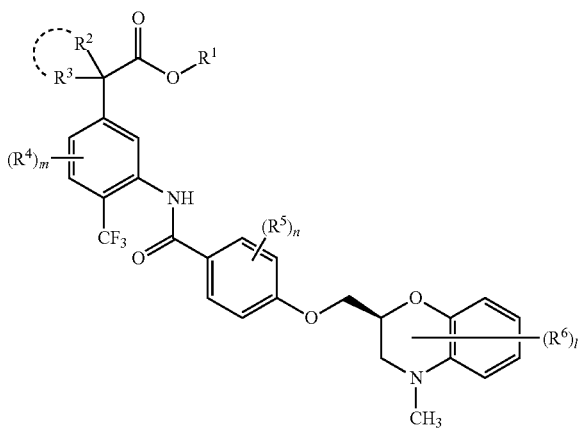

(I)

wherein
$R^1$ represents a hydrogen atom or C1-4 alkyl group,
$R^2$ and $R^3$ each independently represents a hydrogen atom, optionally oxidized C1-4 alkyl group or optionally protected hydroxyl group, with the proviso that $R^2$ and $R^3$ do not represent an optionally protected hydroxyl group at the same time, or $R^2$ and $R^3$ taken together represent optionally oxidized C2-5 alkylene group,
$R^4$, $R^5$ and $R^6$ each independently represents a halogen atom, optionally oxidized C1-6 alkyl group, optionally protected hydroxyl group, trihalomethyl group, —$SO_2R^7$ group, —$SOR^7$ group, or —$SR^7$ group,
$R^7$ represents C1-6 alkyl group or optionally substituted phenyl group, indicates that the substituent is attached in front of the sheet,
m represents 0 or an integer from 1 to 3,
n represents 0 or an integer from 1 to 4, and
i represents 0 or an integer from 1 to 7, with the proviso that when m is 2 or more, $R^4$ may be the same or different, when n is 2 or more, a $R^5$ may be the same or different, and when i is 2 or more, $R^6$ may be the same or different,
a salt thereof, an N-oxide thereof or a solvate thereof, or a prodrug thereof;
(2) the compound according to (1), wherein $R^2$ and $R^3$ taken together represent a C2-5 alkylene group;
(3) the compound according to (1), wherein $R^2$ is a hydroxyl group, and $R^3$ is a hydrogen atom or optionally oxidized C1-4 alkyl group;
(4) the compound according to (1), wherein $R^2$ and $R^3$ are hydrogen atoms;
(5) a compound selected from a group comprising
(1) 1-(3-((2,6-dimethyl-4-(((2S)-4-methyl-3,4-dihydro-2H-1,4-benzoxazin-2-yl)methoxy)benzoyl)amino)-4-(trifluoromethyl)phenyl)cyclopropanecarboxylic acid,
(2) 1-(3-((2-ethyl-4-(((2S)-4-methyl-3,4-dihydro-2H-1,4-benzoxazin-2-yl)methoxy)benzoyl)amino)-4-(trifluoromethyl)phenyl)cyclopropanecarboxylic acid,
(3) 1-(3-((2-ethyl-6-methyl-4-(((2S)-4-methyl-3,4-dihydro-2H-1,4-benzoxazin-2-yl)methoxy)benzoyl)amino)-4-(trifluoromethyl)phenyl)cyclopropanecarboxylic acid,
(4) (3-((2,6-dimethyl-4-(((2S)-4-methyl-3,4-dihydro-2H-1,4-benzoxazin-2-yl)methoxy)benzoyl)amino)-4-(trifluoromethyl)phenyl)acetic acid,
(5) (3-((2-ethyl-6-methyl-4-(((2S)-4-methyl-3,4-dihydro-2H-1,4-benzoxazin-2-yl)methoxy)benzoyl)amino)-4-(trifluoromethyl)phenyl)acetic acid,
(6) hydroxy(3-((2,6-dimethyl-4-(((2S)-4-methyl-3,4-dihydro-2H-1,4-benzoxazin-2-yl)methoxy)benzoyl)amino)-4-(trifluoromethyl)phenyl)acetic acid, and
(7) 2-hydroxy-2-(3-((2,6-dimethyl-4(((2S)-4-methyl-3,4-dihydro-2H-1,4-benzoxazin-2-yl)methoxy)benzoyl)amino)-4-(triflouromethyl)phenyl)propionic acid,
a salt thereof, an N-oxide thereof or a solvate thereof, or a prodrug thereof;
(6) a pharmaceutical composition comprising the compound represented by formula (I) according to (1), a salt thereof, an N-oxide thereof or a solvate thereof, or a prodrug thereof as an active ingredient;
(7) the pharmaceutical composition according to (6), which is a DP receptor antagonist;
(8) the pharmaceutical composition according to (6), which is a drug for prevention and/or treatment of the diseases mediated by the DP receptors;
(9) the pharmaceutical composition according to (8), in which the diseases mediated by the DP receptors are allergy disease, systemic mastocytosis, disorders accompanied by systemic mast cell activation, anaphylaxis shock, bronchoconstriction, urticaria, eczema, acne, allergic bronchial pulmonary aspergillosis, sinusitis, migraine, nasal polypus, anaphylactic vasculitis, eosinophilic syndrome, contact dermatitis, diseases accompanied by itch, diseases generated secondarily as a result of behavior accompanied by itch, diseases accompanied by flushing, inflammation, chronic obstructive pulmonary diseases, ischemic reperfusion injury, cerebrovascular accident, autoimmune disease, traumatic brain disorder, hepatopahty, graft rejection, rheumatoid arthritis, pleurisy, osteoarthritis, Crohn's disease, ulcerative colitis, irritable bowel syndrome, interstitial cystitis, muscular dystrophy, polymyositis, cancer, leukemia, viral infection, multiple sclerosis, sleeping disorders, or diseases associated to platelet aggregation;

(10) the pharmaceutical composition according to (9), in which the allergy disease is the allergic rhinitis, allergic conjunctivitis, atopic dermatitis, bronchial asthma, or food allergy;

(11) a medicament comprising a combination of the compound represented by formula (I) according to (1), a salt thereof, an N-oxide thereof or a solvate thereof, or a prodrug thereof and one or more drugs selected from the group consisting of an antihistamine agent, suppressor for mediator liberation, thromboxane synthetase inhibitor, antagonist for thromboxane A2 receptor, antagonist for leukotriene receptor, leukotriene synthase inhibitor, cytokine inhibitor, steroid agent, sympathomimetic agent, phosphodiesterase IV inhibitor, xanthine derivative, anticholinergic agent, anti-IgE antibody formulation, immunosuppressive agent, chemokine receptor antagonist, adhesion molecule inhibitor, other prostanoid receptor antagonist, nonsteroidal anti-inflammatory agent and nitric oxide synthase inhibitor;

(12) a method for prevention and/or treatment of the diseases mediated by the DP receptors, characterized by administering an effective dose of the compound represented by formula (I) according to (1), a salt thereof, an N-oxide thereof or a solvate thereof, or a prodrug thereof to a mammal;

(13) use of the compound represented by formula (I) according to (1), a salt thereof, an N-oxide thereof or a solvate thereof, or a prodrug thereof for production of a medicament for prevention and/or treatment of the diseases mediated by the DP receptors, and

(14) a compound represented by formula (I-a),

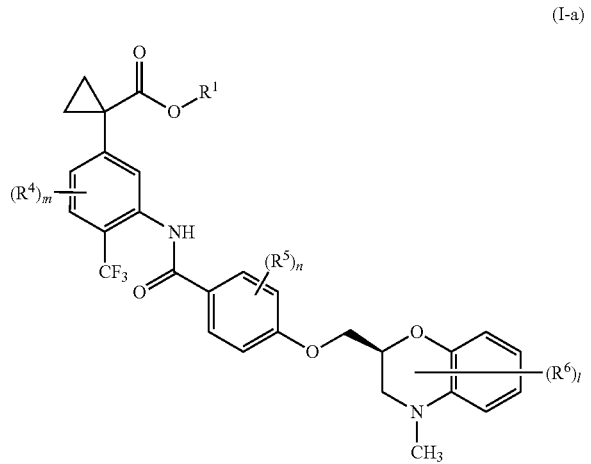

(I-a)

wherein
$R^1$ represents a hydrogen atom or C1-4 alkyl group,
$R^4$, $R^5$, and $R^6$ each independently represents a halogen atom, optionally oxidized C1-6 alkyl group, optionally protected hydroxyl group, trihalomethyl group, —$SO_2R^7$ group, —$SOR^7$ group, or —$SR^7$ group,
$R^7$ represents C1-6 alkyl group or optionally substituted phenyl group,
indicates that the substituent is attached in front of the sheet,
m represents 0 or an integer from 1 to 3,
n represents 0 or an integer from 1 to 4, and
i represents 0 or an integer from 1 to 7, with the proviso that when m is 2 or more, $R^4$ may be the same or different, when n is 2 or more, $R^5$ may be the same or different, and when i is 2 or more, $R^6$ may be the same or different, a salt thereof, an N-oxide thereof or a solvate thereof, or a prodrug thereof.

EFFECT OF THE INVENTION

Since the compound of the present invention represented by formula (I) binds to the DP receptor and behaves as an antagonist, it is useful for prevention and/or treatment of the diseases mediated by the DP receptors. Additionally, since the compound of the present invention represented by formula (I) does not have a strong inhibitory effect against a drug-metabolizing enzyme and has good receptor selectivity against the DP receptors, it can be used as a safe drug.

BEST MODE FOR CARRYING OUT THE INVENTION

In the present specification, $R^1$ represents a hydrogen atom or C1-4 alkyl group.

C1-4 alkyl groups represented by $R^1$ include straight and branched alkyl groups, that is, methyl, ethyl, propyl, isopropyl, butyl, isobutyl, sec-butyl, and tert-butyl groups.

In the present specification, $R^2$ and $R^3$ each independently represents a hydrogen atom, optionally oxidized C1-4 alkyl group or optionally protected hydroxyl group, or $R^2$ and $R^3$ taken together represent optionally oxidized C2-5 alkylene group, Optionally oxidized C1-4 alkyl groups represented by $R^2$ or $R^3$ include C1-4 alkyl group optionally substituted by 1 to 3 hydroxyl groups and/or 1 to 3 oxo groups. Note that the carbon atom to which a plurality of hydroxyl groups and/or oxo groups bind is limited to the terminal carbon atom. Specifically, C1-4 straight or branched alkyl groups comprised of methyl, ethyl, propyl, isopropyl, butyl, isobutyl, sec-butyl, and tert-butyl groups, hydroxymethyl, formyl, carboxy, 2-hydroxyethyl, 2-oxoethyl, carboxymethyl, 1-hydroxyethyl, acetyl, 3-hydroxypropyl, 3-oxopropyl, 2-carboxyethyl, 2-hydroxypropyl, 2-oxopropyl, 1-hydroxy-1-methylethyl, 4-hydroxybutyl, 4-oxobutyl, 3-carboxypropyl, 3-hydroxybutyl, 3-oxobutyl, 3-hydroxy-2-methylpropyl, 22-methyl-3-oxopropyl, 2-carboxypropyl, 2-hydroxy-2-methylpropyl, 3-hydroxy-1-methylpropyl, 1-methyl-3-oxopropyl, 2-carboxy-1-methylethyl, 2-hydroxy-1-methylpropyl, 1-methyl-2-oxopropyl, 1-hydroxy-1-methylpropyl, 1-hydroxmethylpropyl, 1-formylpropyl, 1-carboxypropyl, 2-hydroxy-1,1-dimethylethyl, 1,1-diemthyl-2-oxoethyl, or 1-carboxy-1-methylethyl group are exemplified.

Optionally protected hydroxyl, groups represented by $R^2$ or $R^3$ include a hydroxyl group or a hydroxyl group protected by a protective group. Protective groups of the hydroxyl group include, for example, alkyl groups optionally having a substituent (for example, straight and branched C1-6 alkyl groups such as methyl, ethyl, n-propyl, isopropyl, n-butyl, isobutyl, sec-butyl, tert-butyl, pentyl, hexyl, etc., C7-15 aralkyl groups such as benzyl, phenethyl, phenylpropyl, naphthylmethyl, naphthylethyl, etc.), carbocyclic ring groups that may have a substituent (for example, an optionally, partially or fully saturated. C3-15 monocyclic, bicyclic or tricyclic unsaturated carbon-ring, such as cyclopropane, cyclobutane, cyclopentane, cyclohexane, benzene, toluene, xylene, indene, indane, or naphthalene), heterocyclic groups that may have a substituent (for example, a 3-15 membered monocyclic, bicyclic or tricyclic unsaturated heterocyclic ring containing 1 to 5 heteroatoms selected from oxygen, nitrogen, and sulfur atoms, such as pyrrole, imidazole, triazole, tetrazole, pyrazole, pyridine, pyrazine, pyrimidine, furan, thiophene, oxazole, isoxazole, thiazole, oxadiazole, oxazine, oxadiazin, thiadiazole, indole, benzofuran, benzothiophene, quinoline, isoquinoline, benzoxazole, benzothiazole, or benzimidazole, or an optionally, partially or fully saturated 3-15 membered monocyclic, bicyclic or tricyclic unsaturated heterocyclic ring containing 1 to 5 heteroatoms selected from oxygen, nitrogen, and sulfur atoms, such as aziridine, azetidine, pyrrolidine, piperidine, piperazine, oxirane, oxetane, tetrahydrofuran, tetrahydropyran, morpholine, indoline, or dihydrobenzofuran), alkylsulfonyl groups (for example, a C1-4 alkylsulfonyl group such as methylsulfonyl, ethylsulfonyl, etc.,), arylsulfonyl groups (for example, C6-10 arylsulfonyl group such as phenylsulfonyl), or acyl groups (for example, C1-6 alkanoyl group such as formyl, acetyl, propanoyl, pivaloyl, and, for example, C6-10 arylcarbonyl group such as benzoyl).

Optionally oxidized C2-5 alkylene groups represented by $R^2$ and $R^3$ taken together include, C2-5 straight and branched alkylene groups, such as ethylene, propylene, isopropylene, butylene, isobutylene, and pentylene, which are optionally substituted by 1 to 3 hydroxyl groups and/or 1 to 3 oxo groups. Specifically, $-(CH_2)_2-$, $-(CH_2)_3-$, $-CH_2CH(CH_3)-$, $-(CH_2)_4-$, $-(CH_2)_2CH(CH_3)-$, $-CH_2CH(CH_3)CH_2-$, $-CH(CH_3)CH(CH_3)-$, $-CH_2CH(CH_3)_2-$, $-(CH_2)_5-$, $-(CH_2)_3CH(CH_3)-$, $-(CH_2)_2CH(CH_3)CH_2-$, $-CH_2CH(OH)-$, $-CH_2C(O)-$, $-CH_2CH_2CH(OH)-$, $-CH_2CH(OH)CH_2-$, $-CH_2CH_2C(O)-$, $-CH_2C(O)CH_2-$, etc. are exemplified.

In the present specification, $R^4$ is a halogen atom, optionally oxidized C1-6 alkyl group, optionally protected hydroxyl group, trihalomethyl group, $-SO_2R^7$ group, $-SOR^7$ group, or $-SR^7$ group.

Halogen atoms represented by $R^4$ include fluorine, chlorine, bromine, and iodine atom.

Optionally oxidized C1-6 alkyl groups represented by $R^4$ include C1-6 alkyl groups optionally substituted by 1 to 3 hydroxyl groups and/or 1 to 3 oxo groups. Note that the carbon atom to which a plurality of hydroxyl groups and/or oxo groups bind is limited to the terminal carbon atom. Specifically, a C1-6 straight or branched alkyl group such as methyl, ethyl, propyl, isopropyl, butyl, isobutyl, sec-butyl, tert-butyl, pentyl, isopentyl, neopentyl, hexyl, or isohexyl group, hydroxymethyl, formyl, carboxy, 2-hydroxyethyl, 2-oxoethyl, carboxymethyl, 1-hydroxyethyl, acetyl, 3-hydroxypropyl, 3-oxopropyl, 2-carboxyethyl, 2-hydroxypropyl, 2-oxopropyl, 1-hydroxy-1-methylethyl, 4-hydroxybutyl, 4-oxobutyl, 3-carboxypropyl, 3-hydroxybutyl, 3-oxobutyl, 3-hydroxy-2-methylpropyl, 2-methyl13-oxopropyl, 2-carboxypropyl, 2-hydroxy-2-methylpropyl, 3-hydroxy-1-methylpropyl, 1-methyl-3-oxopropyl, 2-carboxy-1-methylethyl, 2-hydroxy-1-methylpropyl, 1-methyl-2-oxopropyl, 1-hydroxy-1-methylpropyl, 1-hydroxymethylpropyl, 1-formylpropyl, 1-carboxypropyl, 2-hydroxy-1,1-dimethylethyl, 1,1-dimethyl-2-oxoethyl, or 1-carboxy-1-methylethyl group are exemplified.

The optionally protected hydroxyl group represented by $R^4$ and the optionally protected hydroxyl group represented by $R^2$ and $R^3$ has the same meaning.

The trihalomethyl group represented by $R^4$ means a methyl group substituted by 3 halogen atoms, and includes trifluoromethyl, trichloromethyl group, etc.

$R^7$ in $-SO_2R^7$ group, $-SOR^7$ group, or $-SR^7$ group represented by $R^4$ represents a C1-6 alkyl group, or an optionally substituted phenyl group.

C1-6 alkyl groups represented by $R^7$ include straight and branched alkyl groups comprised of methyl, ethyl, propyl, isopropyl, butyl, isobutyl, sec-butyl, tert-butyl, pentyl, isopentyl, neopentyl, hexyl, and isohexyl group.

Optionally substituted phenyl groups represented by $R^7$ include, for example, phenyl group, tolyl group, xylyl group, etc.

In the present specification, $R^5$ represents a halogen atom, optionally oxidized C1-6 alkyl group, optionally protected hydroxyl group, trihalomethyl group, $-SO_2R^7$ group, $-SOR^7$ group, or $-SR^7$ group.

The halogen atom, optionally oxidized C1-6 alkyl group, optionally protected hydroxyl group, and trihalomethyl group represented by $R^5$ respectively have the same meanings as the halogen atom, optionally oxidized C1-6 alkyl group, optionally protected hydroxyl group, and trihalomethyl group represented by $R^4$.

$R^7$ in $-SO_2R^7$ group, $-SOR^7$ group, or $-SR^7$ group represented by $R^5$ represents C1-6 alkyl group, or optionally substituted phenyl group.

In the present specification, $R^6$ is a halogen atom, optionally oxidized C1-6 alkyl group, optionally protected hydroxyl group, trihalomethyl group, $-SO_2R^7$ group, $-SOR^7$ group, or $-SR^7$ group.

The halogen atom, optionally oxidized C1-6 alkyl group, optionally protected hydroxyl group, and trihalomethyl group represented by $P^6$ respectively have the same meanings as the halogen atom, optionally oxidized C1-6 alkyl group, optionally protected hydroxyl group, and trihalomethyl group represented by $R^4$ have the same meanings.

$R^7$ in $-SO_2R^7$ group, $-SOR^7$ group, or $-SR^7$ group represented by $R^6$ represents C1-6 alkyl group, or optionally substituted phenyl group.

In the present specification, m represents 0 or an integer from 1 to 3, with the proviso that when m is 2 or more, $R^4$ may be the same or different.

In the present specification, n represents 0 or an integer from 1 to 4, but when n is 2 or more, $R^5$ may be the same or different.

In the present specification, i represents 0 or an integer from 1 to 7, but when i is 2 or more, $R^6$ may be the same or different.

In the present invention, unless otherwise specifically stated, as will be appreciated by those skilled in the art, the symbol ⋯ indicates that the substituent is attached into the plane of the sheet (that is, α-position), and the symbol ▰ indicates that the substituent is attached in front of the sheet (that is, β-position), and the symbol ╱ indicates the mixture of α-position and β-position.

In formula (I), $R^1$ is preferably a hydrogen atom.

In formula (I), $R^2$ and $R^3$ are preferably a hydrogen atom, C1-4 alkyl group or hydroxyl group, more preferably a hydrogen atom or hydroxyl group.

In formula (I), $R^2$ and $R^3$ together preferably represent a C2-5 alkylene group, more preferably $-(CH_2)_2-$.

In the group

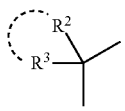

of formula (I), it is preferable that
$R^2$ and $R^3$ taken together represent a C2-5 alkylene group,
$R^2$ and $R^3$ is a combination, wherein $R^2$ is a hydroxyl group and $R^3$ is a hydrogen atom or optionally oxidized C1-4 alkyl group, or
$R^2$ and $R^3$ are hydrogen atoms, and
it is more preferable that
$R^2$ and $R^3$ taken together represent a C2-5 alkylene group, or
$R^2$ and $R^3$ is a combination, wherein $R^2$ is a hydroxyl group and $R^3$ is a hydrogen atom or C1-4 alkyl group.

In formula (I), $R^4$ is preferably a halogen atom, C1-6 alkyl group, hydroxyl group, trihalomethyl group, —$SO_2R^7$ group, —$SOR^7$ group, or —$SR^7$ group, more preferably a halogen atom, or C1-6 alkyl group, particularly preferably a chlorine atom or methyl group.

In formula (I), $R^5$ is preferably a halogen atom, C1-6 alkyl group, hydroxyl group, trihalomethyl group, —$SO_2R^8$ group, —$SOR^8$ group, or —$SR^8$ group, more preferably a halogen atom or C1-6 alkyl group, particularly preferably a chlorine atom, methyl group, ethyl group, or isopropyl group.

In formula (I), $R^6$ is preferably a halogen atom, C1-6 alkyl group, hydroxyl group, trihalomethyl group, —$SO_2R^9$ group, —$SOR^9$ group, or —$SR^9$ group, more preferably a halogen atom or C1-6 alkyl group, particularly preferably a chlorine atom or methyl group.

In formula (I), m is preferably 0 or 1, more preferably 0.

In formula (I), n is preferably 0 or an integer from 1 to 2, more preferably 2.

In formula (I), i is preferably 0 or an integer from 1 to 4, more preferably 0 or an integer from 1 to 2, particularly preferably 0.

Among the compounds represented by formula (I), a compound represented by formula (I-a)

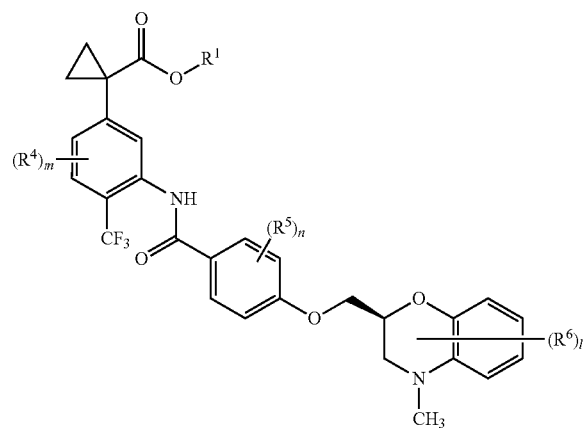

(I-a)

wherein all symbols in the formula have the same meanings hereinbefore, a compound represented by formula (I-b)

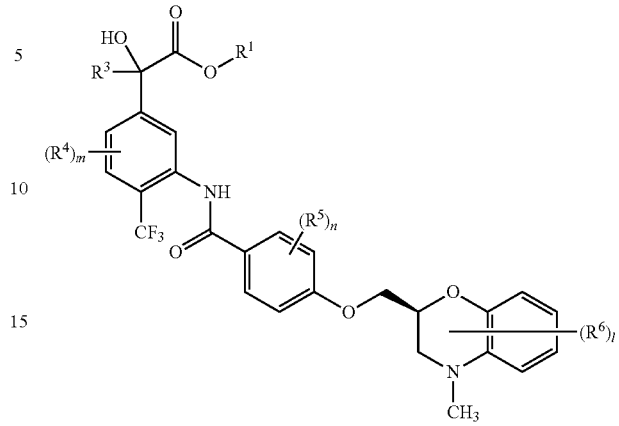

(I-b)

wherein all symbols in the formula have the same meanings hereinbefore, and a compound represented by formula (I-c)

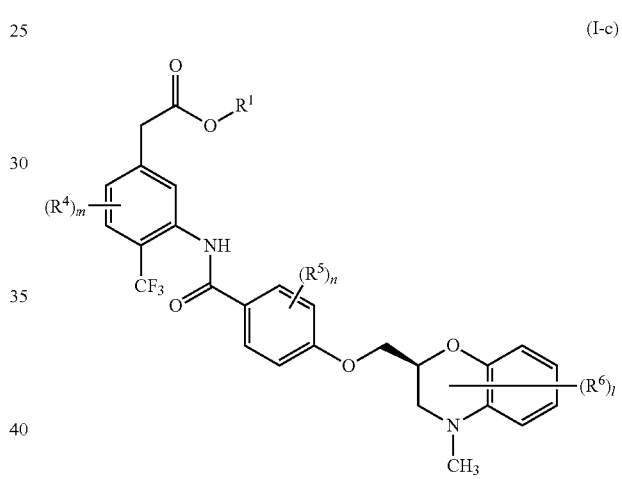

(I-c)

wherein all symbols in the formula have the same meanings hereinbefore, are preferable. Especially, the compound represented by formula (I-a) is preferable.

Among the compounds represented by formula (I), specifically preferable compounds are
(1) 1-3-((2,6-dimethyl-4-(((2S) -4-methyl-3,4-dihydro-2H-1,4-benzoxazin-2-yl)methoxy)benzoyl)amino)-4-(trifluoromethyl)phenyl)cyclopropanecarboxylic acid,
(2) 1-(3-((2-ethyl-4-(((2S)-4-methyl-3,4-dihydro-2H-1,4-benzoxazin-2-yl)methoxy)benzoyl)amino)-4-trifluoromethyl)phenyl)cyclopropanecarboxylic acid,
(3) 1-(3-((2-ethyl-6-methyl-4-(((2S)-4-methyl-3,4-dihydro-2H-1,4-benzoxazin-2-yl)methoxy)benzoyl)amino)-4-(trifluoromethyl)phenyl)phenyl)cyclopropanecarboxylic acid,
(4) (3-((2,6-dimethyl-4-(((2S)-4-methyl-3,4-dihydro-2H-1,4-benzoxazin-2-yl)methoxy)benzoyl)amino)-4-(trifluoromethyl)phenyl)acetic acid,
(5) (3-((2-ethyl-6-methyl-4-(((2S) -4-methyl-3,4-dihydro-2H-1,4-benzoxazin-2-yl)methoxy)benzoyl)amino)-4-(trifluoromethyl)phenyl)acetic acid,
(6) hydroxy(3-((2,6-dimethyl-4-(((2S)-4-methyl-3,4-dihydro-2H-1,4-benzoxazin-2-yl)methoxy)benzoyl)amino) -4-(trifluoromethyl)phenyl)acetic acid, and (7) 2-hydroxy-2-(3-((2,6-dimethyl-4-(((2S)-4-methyl-3,4-dihydro-2H-1,4-benzoxazin-2-yl)methoxy)benzoyl)amino)-4-(trifluoromethyl)phenyl) propionic acid.

In the present invention, unless specifically directed, compounds include all their isomers. For example, alkyl, alkenyl, alkynyl, alkoxy, alkylthio, alkylene, alkenylene, and alkynylene groups include straight and branched types in the present invention. Further, compounds include all their isomers regarding to double bonds, rings, and fuzed rings (E-, Z-, cis-, trans-isomer), isomers regarding to the presence of asymmetrical carbon (R-, S-isomer, α-, β-configurations, enantiomers, diastereomer), optical active isomers having optical rotation (D, L, d, l-isomer), tautomers, polar isomers according to chromatographic separation (more polar isomer, less polar isomer), equilibrium compounds, rotamers, mixtures thereof at any rate, racemic mixtures in the present invention In the present invention, an enantiomer of the compound represented by formula (I), that is, the compound represented by formula (I-E),

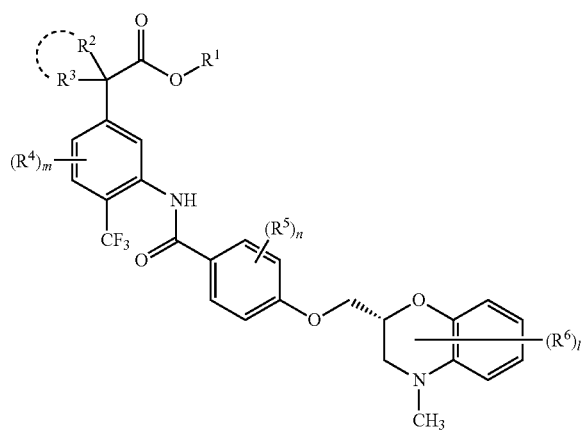

(I-E)

wherein all symbols in the formula have the same meanings hereinbefore may be accompanied to one compound represented by formula (I) provided that the amount of the former compound is less than the amount substantially affecting the effect of the present invention.

The compound represented by formula (I) can be converted to a salt thereof by a conventional method. The salts include alkali metal salts, alkaline-earth metal salts, ammonium salts, amine salts, and acid addition salts. It is preferable that the salt is pharmaceutically acceptable.

The salt is preferably water-soluble. The suitable salts include salts of alkali metal (potassium, sodium, etc.), salts of alkaline earth metal (calcium, magnesium, etc.), ammonium, pharmaceutically acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine, etc).

The acid addition salt is preferably water-soluble. The suitable acid addition salts include, for example, inorganic acid salts such as a hydrochloride, hydrobromide, hydroiodide, sulfate, phosphate, nitrate, etc., or organic acid salts such as an acetate, lactate, tartrate, benzoate, citrate, methanesulfonate, ethanesulfonate, benzenesulfonate, toluenesulfonate, isethionate, glucuronate, gluconate, etc.

The compound of the present invention can be converted into the N-oxide thereof by an arbitrary method. An N-oxide is a compound in which a nitrogen atom in the compound represented by formula (I) is oxidized.

The compounds represented by formula (I) and the salts thereof can be converted to the solvates thereof.

The solvates are preferably nontoxic and water-soluble. Appropriate solvates include, for example, solvates of water or alcohol solvents (for example, ethanol, etc.).

A prodrug of the compound represented by formula (I) denotes the compound which is converted to a compound represented by formula (I) by a reaction with an enzyme, stomach acid, etc. in vivo. Prodrugs of the compound represented by formula (I) include, when the compounds represented by formula (I) have a hydroxyl group, the compounds whose hydroxyl group is acylated, alkylated, phosphorylated, or borated (for example, the compounds represented by formula (I) whose hydroxyl group is acetylated, palmitoylated, propanoylated, pivaloylated, succinylated, fumarylated, alanylated, or dimethylaminomethylcarbonylated);

when the compounds represented by formula (I) have a carboxyl group, the compounds whose carboxyl group is esterified or amidated (for example, the compounds represented by formula (I) whose carboxyl group is made into ethyl ester, isopropyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, or methylamide); and when the compounds represented by formula (I) have a carboxyl group, the compounds whose carboxyl group is replaced by a hydroxymethyl group.

These compounds can be prepared by methods known per se. Additionally, the prodrug of the compound represented by formula (I) may be either a hydrate or non-hydrate thereof.

Method for Preparation of the Compound of the Present Invention

The compounds of the present invention represented by formula (I) can be prepared by conventional methods, such as methods shown below, methods analogous thereto, or methods given in the example. Note that, in each preparation method shown below, the starting compound may be in the form of salt. Such salts include one described above as pharmaceutically acceptable salts of formula (I).

[I] Among the compounds represented by formula (I), the compounds whose $R^1$ represents C1-4 alkyl group, that is, the compounds represented by formula (IA)

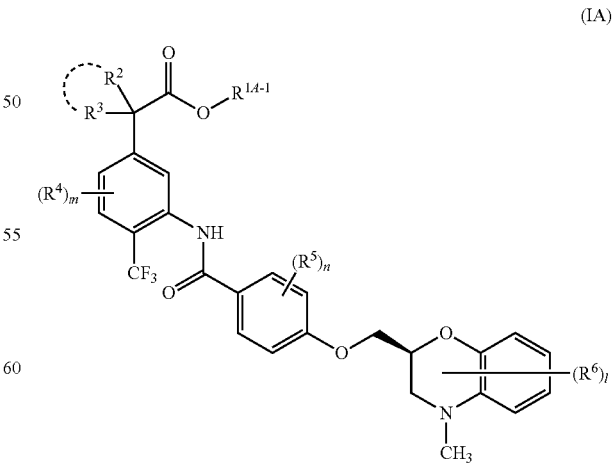

(IA)

wherein $R^{1A-1}$ represents C1-4 alkyl group, and other symbols have the same meanings hereinbefore, can be prepared by the method shown below.

The compounds represented by formula (IA) can be prepared by subjecting the compounds represented by formula (II)

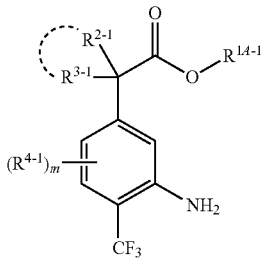

wherein $R^{2-1}$, $R^{3-1}$, and $R^{4-1}$ respectively have the same meanings as $R^2$, $R^3$, and $R^4$, in which, carboxyl group or hydroxyl group in the group represented by $R^{2-1}$, $R^{3-1}$, and $R^{4-1}$ is protected, if necessary, and other symbols have the same meanings hereinbefore,
and the compounds represented by formula (III)

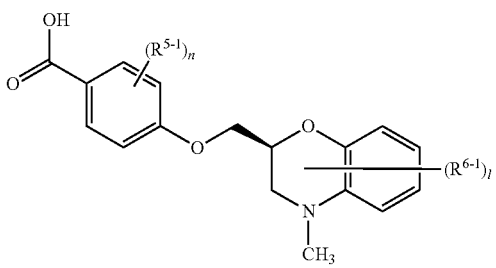

wherein $R^{5-1}$ and $R^{6-1}$ respectively have the same meanings as $R^5$ and $R^6$, in which, carboxyl group or hydroxyl group in a group represented by $R^{5-1}$ and $R^{6-1}$ is protected, if necessary, and other symbols have the same meanings hereinbefore, to amidation reaction, followed by deprotection reaction, if necessary.

The amidation reactions are publicly known, and include, for example,
(1) a method using an acid halide
(2) a method using a mixed acid anhydride, and
(3) a method using a condensation agent.

These methods are specifically described below:

(1) The method using an acid halide is carried out, for example, as described below: A carboxylic acid is reacted with an acid halogenating agent (oxalyl chloride, thionyl chloride, etc) in an organic solvent (chloroform, dichloromethane, diethyl ether, tetrahydrofuran, dimethoxyethane, acetonitrile, ethyl acetate, toluene, etc) or in the absence of any solvent at −20° C. to reflux temperature, and then the obtained acid halide is reacted with an amine in the presence or absence of a base (pyridine, triethylamine, dimethylaniline, dimethylaminopyridine, diisopropylethylamine, N-methylmorpholine, 5-ethyl-2-methylpyridine (MEP), etc) in an organic solvent (chloroform, dichloromethane, diethyl ether, tetrahydrofuran, acetonitrile, ethyl acetate, etc) at 0 to 40° C. The reactions are preferably carried out under an inert gas (argon, nitrogen, etc.) atmosphere in anhydrous conditions. Additionally, the obtained acid halide may be reacted with an amine using an alkaline aqueous solution (sodium bicarbonate water or sodium hydroxide solution, etc) in the presence or absence of a phase-transfer catalyst (quaternary ammonium salts such as tetrabutylammonium chloride, triethylbenzylammonium chloride, tri-n-octylmethylammonium chloride, trimethyldecylammonium chloride, tetramethylammonium bromide, etc.) in an organic solvent (dioxane, tetrahydrofuran, dichloromethane, etc) at 0 to 40° C.

(2) The method using a mixed acid anhydride is carried out, for example, as described below: A carboxylic acid is reacted with an acid halide (pivaloyl chloride, tosyl chloride, mesyl chloride, etc.) or an acid derivative (ethyl chloroformate, isobutyl chloroformate, etc.) in the presence of a base (pyridine, triethylamine, dimethylaniline, dimethylaminopyridine, diisopropylethylamine, etc.) in an organic solvent (chloroform, dichloromethane, diethyl ether, tetrahydrofuran, etc.) or in the absence of any solvent at 0 to 40° C., and then the obtained mixed acid anhydride is reacted with an amine in an organic solvent (chloroform, dichloromethane, diethyl ether, tetrahydrofuran, etc.) at 0 to 40° C. The reactions are preferably carried out under an inert, gas (argon, nitrogen, etc.) atmosphere in anhydrous conditions.

(3) The method using a condensing agent is carried out, for example, as described below: A carboxylic acid is reacted with an amine in an organic solvent (chloroform, dichloromethane, dimethyl formamide, diethyl ether, tetrahydrofuran, etc.) or in the absence of any solvent at 0 to 40° C. in the presence or absence of a base (pyridine, triethylamine, dimethylaniline, dimethylaminopyridine, etc.), using a condensing agent (1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridiniumiodine, 1-propylphosphonic acid cyclic anhydride (1-propanephosphonic acid cyclic anhydride, PPA), etc.) and using, or not using, 1-hydroxybenztriazole (HOBt). The reactions are preferably carried out under an inert gas (argon, nitrogen, etc.) atmosphere in anhydrous conditions.

The deprotection reaction of a protective group of the carboxyl group or hydroxyl group is well known, and include, for example,
(1) an alkali hydrolysis
(2) a deprotection reaction in an acidic condition,
(3) a deprotection reaction by hydrogenolysis,
(4) a deprotection reaction of silyl group,
(5) a deprotection reaction using metal, and
(6) a deprotection reaction using metal complex.

These methods are specifically described below;

(1) A deprotection reaction by alkali hydrolysis is carried out, for example, by using an alkali metal hydroxide (sodium hydroxide, potassium hydroxide, lithium hydroxide, etc), an alkaline earth metal hydroxide(barium hydroxide, calcium hydroxide, etc), or a carbonate(sodium carbonate, potassium carbonate, etc), or the solution thereof or the mixture thereof in an organic solvent (methanol, tetrahydrofuran, dioxane, etc.) at 0 to 80° C., (2) A deprotection reaction in an acidic condition is carried out, for example, in an organic acid (acetic acid, trifluoroacetic acid, methanesulfonic acid, p-tosylic acid, etc) or inorganic acid (hydrochloric acid, sulfuric acid, etc), or the mixture thereof (hydrogen bromide/acetic acid, etc), in an organic solvent (dichloromethane, chloroform, dioxane, ethyl acetate, anisole, etc) in the presence or absence of 2,2,2-trifluoroethanol, at 0 to 100° C.

(3) A deprotection reaction by hydrogenolysis is carried out, for example, in the presence of catalyst (palladium-carbon, palladium black, palladium hydroxide-carbon, platinum oxide, Raney nickel, etc), under ordinary or increased pressure, in hydrogen atmosphere or in the presence of ammonium formate, in a solvent (ethers(tetrahydrofuran, dioxane, dimethoxyethane, diethyl, ether, etc), alcohols (methanol, ethanol, etc), benzenes(benzene, toluene, etc), ketones(acetone, methyl ethyl ketone, etc), nitrites(acetonitrile, etc), amides(dimethylformamide, etc), water, ethyl acetate, acetic acid, or a mixed solvent comprising two or more thereof, etc), at 0 to 200° C.

(4) A deprotection reaction of silyl group is carried out, for example, using tetrabutylammonium fluoride, in an organic solvent miscible with water (tetrahydrofuran, acetonitrile, etc), at 0 to 40° C.

(5) A deprotection reaction using metal is carried out, for example, in an acidic solvent (acetic acid, buffer solution of pH4.2 to 7.2, or mixed liquid of these solution with an organic solvent such as tetrahydrofuran), in the presence of zinc powder, using ultrasonic waves if needed, at 0 to 40° C.

(6) A deprotection reaction using a metal complex is carried out, for example, using a metal complex (tetrakistriphenylphosphine palladium (0), bis(triphenylphosphine)palladium (II) dichloride, palladium (II) acetate, tris(triphenylphosphine) rhodium (I) chloride, etc), in the presence of a trap reagent (tributyltin hydride, triethylsilane, dimedone, morpholine, diethylamine, pyrrolidine, etc), organic acid (acetic acid, formic acid, 2-ethylhexanoic acid, etc), and/or organic acid, salts (sodium 2-ethylhexanoate potassium 2-ethylhexanoate, etc), in the presence or absence of a phosphine agent (triphenyl phosphine, etc) in an organic solvent (dichloromethane, dimethylformamide, tetrahydrofuran, ethyl acetate, acetonitrile, dioxane, ethanol, etc), water, or mixed solvent thereof, at 0 to 40° C.

The deprotection reaction can be carried out by other methods than those mentioned above, such as the one described in T. W. Greene, Protective Groups in Organic Synthesis, Wiley, N.Y., 1999.

Protective groups of the carboxyl group include, for example, methyl, ethyl, allyl, t-butyl, trichloroethyl, benzyl (Bn), phenacyl, p-methoxybenzyl, trityl, or 2-chlorotrityl group, or a solid phase carrier to which these structures bind.

Protective groups of the hydroxyl group include, for example, methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), t-butyldimethylsilyl (TBDMS), t-butyldiphenylsilyl (TBDPS), acetyl(Ac), pivaloyl, benzoyl, benzyl(Bn), p-methoxybenzyl, allyloxycarbonyl (Alloc), 2,2,2-trichloroethoxycarbonyl (Troc) group, etc.

Protective groups of the carboxyl group or hydroxyl group are not specifically limited to those described above, if they can be easily and selectively eliminated. For example, the protective groups described in T. W. Greene, Protective Groups in Organic Synthesis, Wiley, N.Y., 1999 can be used.

As will be easily understood by those skilled in the art, the target compound of the present invention can be easily prepared by using a deprotection reaction carefully selected for the object.

[II] Among the compounds represented, by formula (I), the compounds whose $R^1$ represents a hydrogen atom, that is, the compound represented by formula (IB)

(IB)

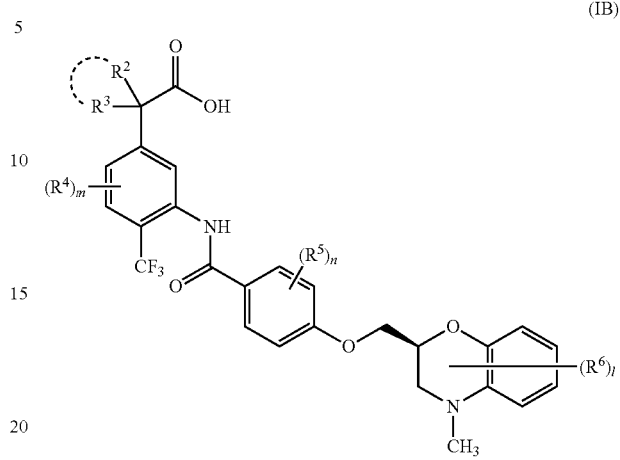

wherein all symbols in the formula have the same meanings hereinbefore, can be prepared by subjecting the compound represented by formula (IA) to a deprotection reaction of the protective group of the carboxyl group, followed by, if necessary, subjecting to a deprotection reaction of the protective group of the hydroxyl group.

The deprotection reaction of the protective group of the carboxyl group can be carried out by the method mentioned above.

As will be easily understood by those skilled in the art, the target compound of the present invention can be easily prepared by using a deprotection reaction carefully selected for the object.

The deprotection reaction of the protective group of the hydroxyl group can be carried out by a method similar to that described above.

The compounds represented by formula (II) and (III) are ones known per se or easily prepared by a conventional method.

For example, among the compounds represented by formula (II), the compounds whose $R^{2-1}$ and $R^{3-1}$ taken together represent a C2-5 alkylene group, that is, the compound represented by formula (II-1), and the compounds whose $R^{2-1}$ and $R^{3-1}$ are hydrogen atoms, that is, the compound represented by formula (II-2), can be prepared by the method represented, by reaction scheme 1 shown below. In reaction scheme 1, $X^1$ and $X^2$ respectively represents independently a halogen atom, j represents an integer from 2 to 5, ring E represents C3-6 membered cycloalkane ring, and other symbols have the same meanings as those previously described.

Reaction Scheme 1

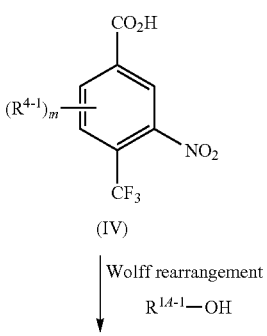

(IV)

Wolff rearrangement $R^{1A-1}$—OH

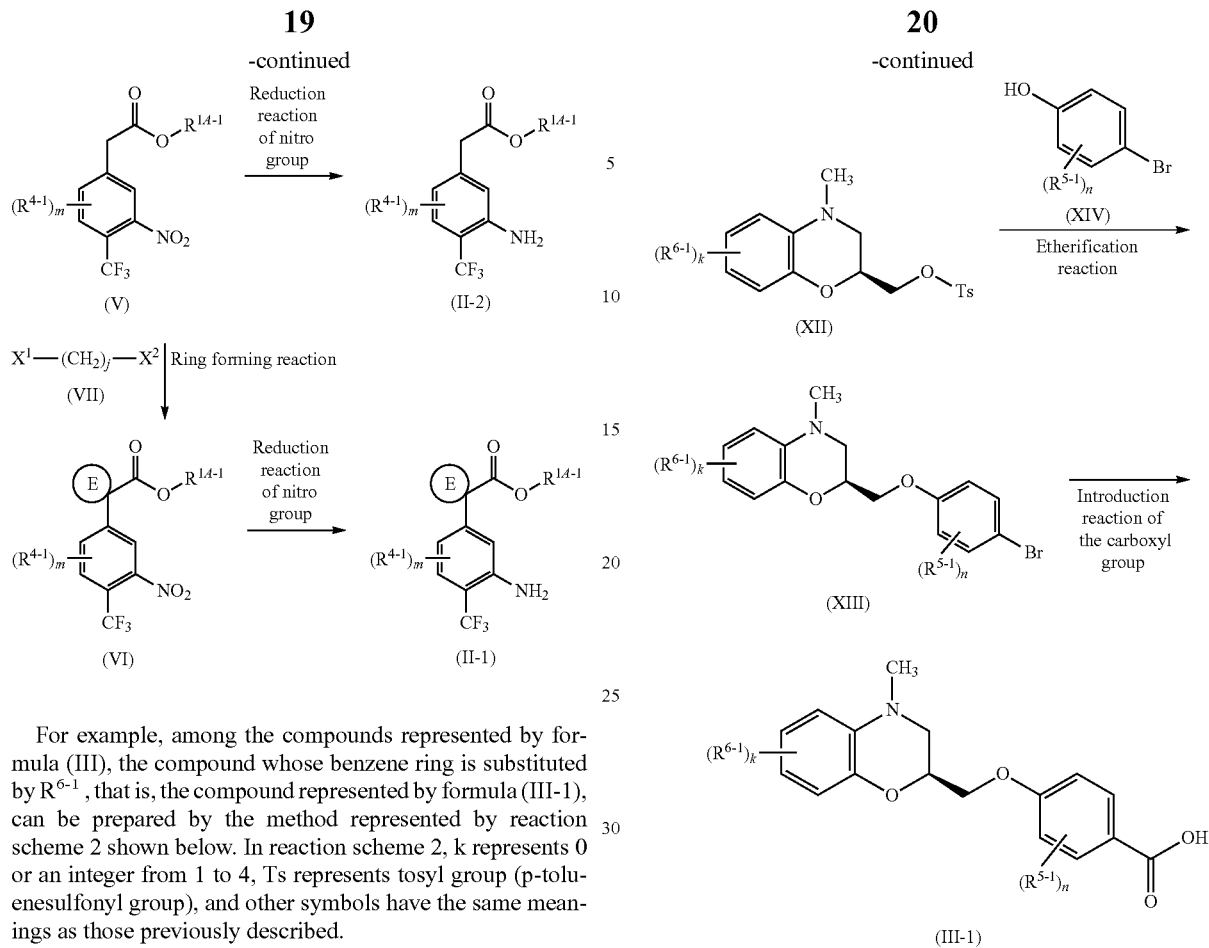

For example, among the compounds represented by formula (III), the compound whose benzene ring is substituted by $R^{6-1}$, that is, the compound represented by formula (III-1), can be prepared by the method represented by reaction scheme 2 shown below. In reaction scheme 2, k represents 0 or an integer from 1 to 4, Ts represents tosyl group (p-toluenesulfonyl group), and other symbols have the same meanings as those previously described.

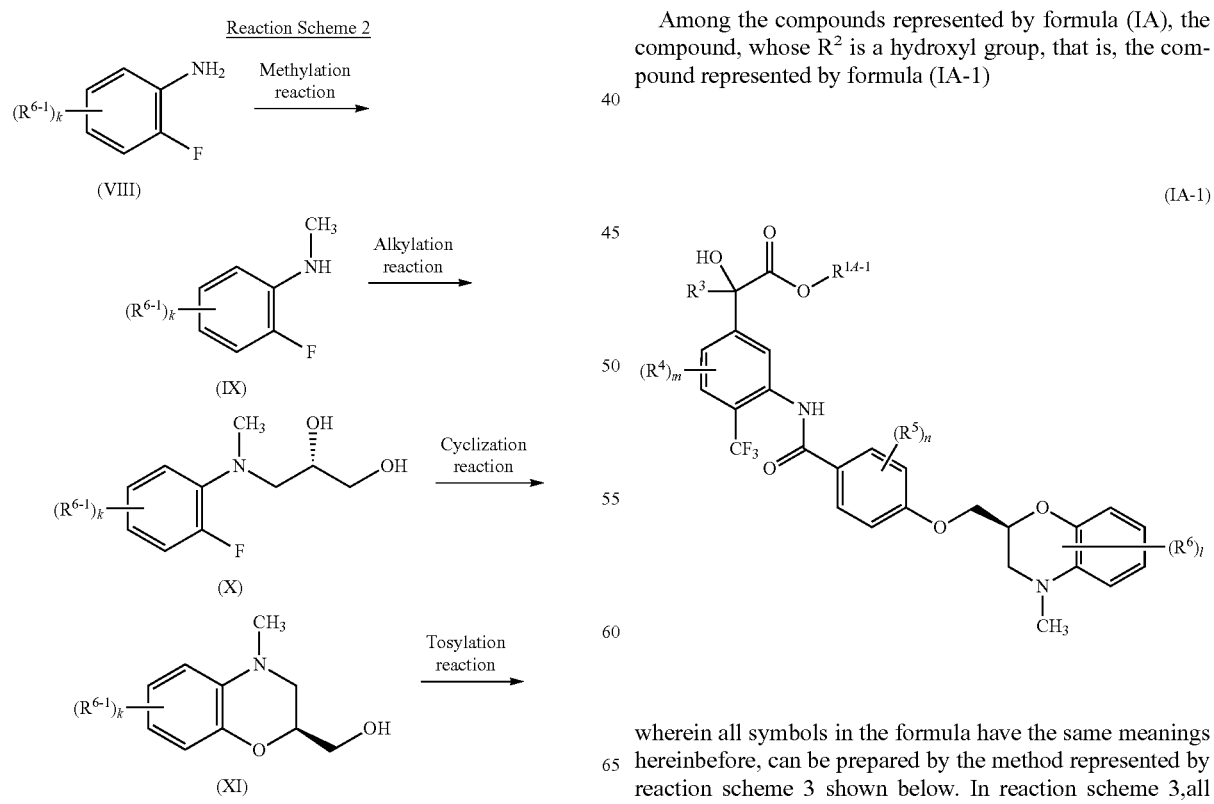

Among the compounds represented by formula (IA), the compound, whose $R^2$ is a hydroxyl group, that is, the compound represented by formula (IA-1)

wherein all symbols in the formula have the same meanings hereinbefore, can be prepared by the method represented by reaction scheme 3 shown below. In reaction scheme 3, all symbols have the same meanings hereinbefore.

Reaction Scheme 3

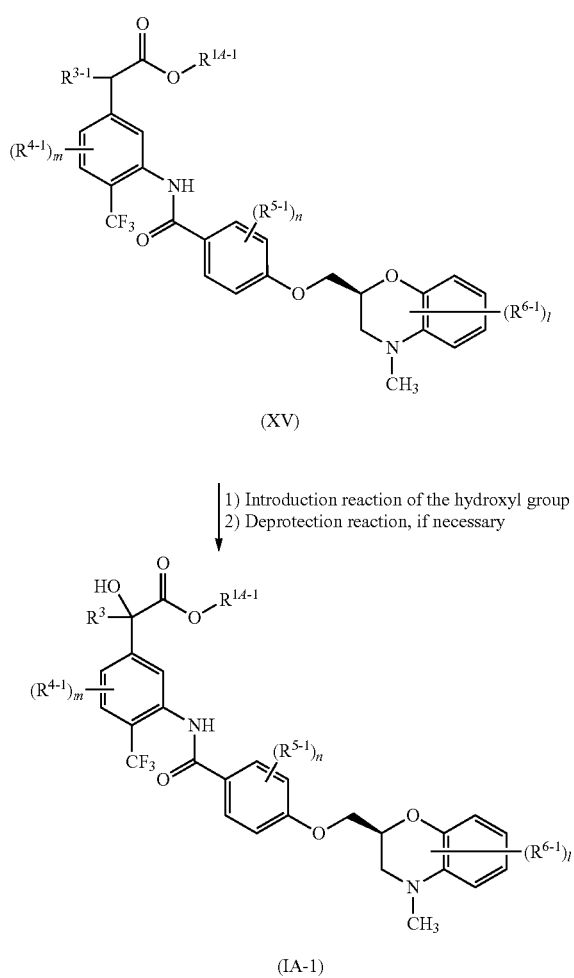

(XV)

1) Introduction reaction of the hydroxyl group
2) Deprotection reaction, if necessary (IA-1)

Among the compounds represented by formula (IB), the compound whose $R^2$ is a hydroxyl group, that is, the compounds represented by formula (IB-1)

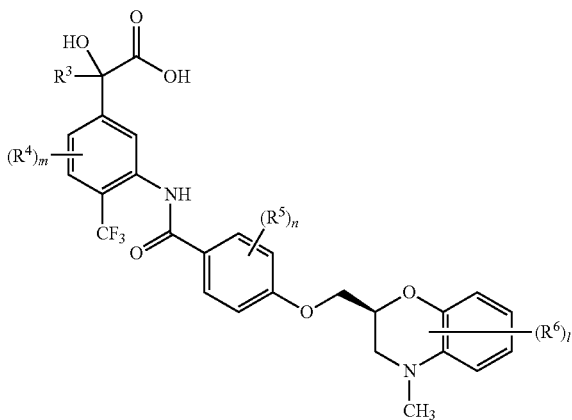

(IB-1)

wherein all symbols in the formula have the same meanings hereinbefore, can be prepared by subjecting the compound represented by formula (IA-1) to a deprotection reaction of the protective group of the carboxyl group, followed by, if necessary, subjecting to a deprotection reaction of the protective group of the hydroxyl group.

The deprotection reaction of the protective group of the carboxyl group can be carried out by the above-mentioned method.

Among the reaction schemes 1 to 3, the compounds represented by formulae (IV), (VII), (VIII), (XIV), and (XV), which are used as the starting materials, are publicly known, or can be easily prepared, by a combination of publicly known methods, for example, methods described, in "Comprehensive Organic Transformations: A Guide to Functional Group Preparations 2nd Edition (Richard C. Larock, John Wiley & Sons Inc, 1999)", or methods described in the examples.

Among the compounds of the present invention described by formula (I), those which are not shown above can be prepared by a combination of methods described in the examples or publicly known methods, for example, methods described in "Comprehensive Organic Transformations: A Guide to Functional Group Preparations 2nd Edition(Richard C. Larock, John Wiley & Sons Inc, 1999)".

In each reaction described in the present specification, the reaction with heating can be carried out, as will be appreciated by those skilled in the art, by using a water bath, oil bath, sand bath, or microwave.

In each reaction described in the present specification, a solid-phase supported reagent attached to a polymer (for example, polystyrene, polyacrylamide, polypropylene, polyethylene glycol, etc) may be appropriately used.

In each reaction described in the present specification, the reaction product can be purified by conventional purification methods, such as distillation under ordinary or decreased pressure, high-performance liquid chromatography using silica gel or magnesium silicate, thin-layer chromatography, ion-exchange resin, scavenger resin or column chromatography, or washing or recrystallization. Purification may be carried out at each reaction or after some reactions.

Application to Medicaments

Since the compound of the present invention represented by formula (I) binds to the DP receptors and acts as an antagonist, it appears to be useful for prevention and/or treatment of diseases mediated by the DP receptors, such as an allergy disease (for example, allergic rhinitis, allergic conjunctivitis, atopic dermatitis, bronchial asthma, food allergy, etc), systemic mastocytosis, disorders accompanied by systemic mast cell activation, anaphylaxis shock, bronchoconstriction, urticaria, eczema, acne, allergic bronchial pulmonary aspergillosis, sinusitis, migraine, nasal polypus, anaphylactic vasculitis, eosinophilic syndrome, contact dermatitis, diseases accompanied by itch(for example, atopic dermatitis, urticaria, allergic conjunctivitis, allergic rhinitis, contact dermatitis, etc), diseases (for example, cataract, retinal detachment, inflammation, infection and sleeping disorders) which are generated secondarily as a result of behavior accompanied by itch (for example, scratching and beating), diseases accompanied by flushing, inflammation, chronic obstructive pulmonary diseases, ischemic reperfusion injury, cerebrovascular accident, autoimmune disease, traumatic brain disorder, hepatopahty, graft rejection, rheumatoid arthritis, pleurisy, osteoarthritis, Crohn's disease, ulcerative colitis, irritable bowel syndrome, interstitial cystitis, muscular dystrophy, polymyositis, cancer, leukemia, viral infection (for example, chronic hepatitis C liver disease, etc), or multiple sclerosis. Additionally, since the receptor is involved in sleep or platelet aggregation, the compound also appears to be useful against diseases relevant to the same.

The compound represented by formula (I) retains or increases the significant DP receptor antagonistic activity, while not strongly inhibiting the drug-metabolizing enzyme, and has good selectivity to DP receptors. Additionally, in respect of the compound represented by formula (I) wherein $R^2$ and $R^3$ taken together represent a C2-5 alkylene group, or $R^2$ represents a hydroxyl group, its effect is remarkable.

Especially, when the compound represented by formula (I-a)

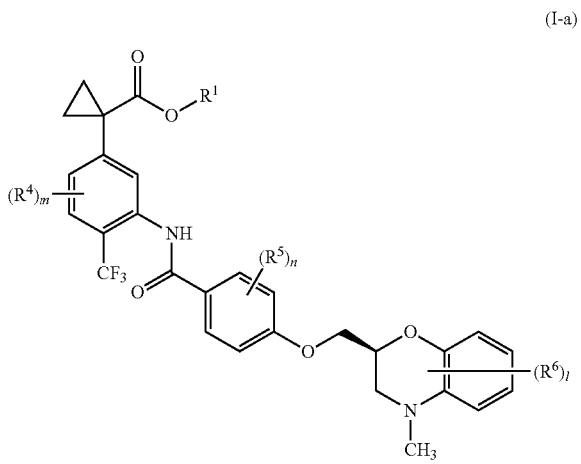

(I-a)

wherein all symbols in the formula have the same meanings hereinbefore has —$(CH_2)_2$— which is represented by $R^2$ and $R^3$ together, the effect is remarkable.

Since the compound of the present invention represented by formula (I) does not have a strong inhibitory effect against drug-metabolizing enzyme such as CYP3A4 or CYP2C9, the compound does not interact pharmaceutically with companion drugs, and therefore, can be used as a safe drug which does not cause serious side-effects.

The inhibitory activity ($IC_{50}$ value) of the compound of the present invention against a drug-metabolizing enzyme is preferably 5 µmol/L or more, more preferably 10 µmol/L or more, especially preferably 30 µmol/L or more.

The arachidonic acid cascade include many types of prostaglandins. Each compound corresponds to a number of prostaglandin receptors, including subtypes thereof, which respectively relate to different pharmacological effects. Therefore, in order to generate a safe drug having a reduced side-effects, it is important that the drug is sufficiently selective to other prostaglandin receptors.

Since the compound of the present invention represented by formula (I) has very high selectivity to the DP receptors, the pharmacological effects mediated by the prostaglandin receptors other than the DP receptors, such as the $EP_1$ receptor, $EP_2$ receptor, $EP_3$ receptor, $EP_4$ receptor, EP receptor, IP receptor, or IP receptor, etc., are not expressed, and therefore, the compound can be used as a safe drug having a reduced side-effects. Note that the effect against the prostaglandin receptors other than the DP receptors can be measured by, for example, the method described in "Biochim. Biophys. Acta., vol. 1483, 2000 (285-293)", etc., or the method described hereinafter in the biological example 3.

The compounds of the present invention represented by formula (I) have high solubility and absorption properties. These are the most required physical, chemical, and pharmacological properties (see "The Merck Manual, of Diagnosis and Therapy ($17^{th}$, Ed.), Merck & Co.") when developing a medicament, and therefore, the compounds of the present invention satisfy the condition required for an excellent medicament.

[Toxicity]

The compound represented by formula (I) has very low toxicity (for example, cellular toxicity, hepatotoxicity, nephrotoxicity, respiratory toxicity, brain and neurotoxicity, gastrointestinal toxicity, cardiovascular toxicity, hematological and hematopoietic toxicity, immunotoxicity, osteocartilaginous tissue toxicity, dermal toxicity, sense organ toxicity, reprotoxy and genital toxicity, endocrine toxicity, teratogenesis, carcinogenicity, or mutagenicity) and is safe enough for pharmaceutical use.

The compound represented by formula (I), pharmaceutically acceptable salt thereof, or solvate thereof may be administered as a companion drug in combination with other drugs for the purposes of
(1) complementation and/or enhancement of preventive and/or therapeutic effects of the therapeutic substance of the present invention,
(2) improvement of pharmacokinetics and absorption of the therapeutic substance of the present invention and reduction of the dosage, and/or
(3) reduction of side effects of the therapeutic substance of the present, invention.

The drug of the present invention in combination with other drugs may be administered in the form of a formulation comprising both components in single formulation, or may be administered in the form of separate formulations. Administration in the form of separate formulations includes simultaneous administration and time lag administration. In case of time lag administration, the other drugs may be administered after the administration of the compound of the present invention, or the drug of the present invention may be administered after the administration of the other drugs. Respective administration methods may be the same or different.

The above-mentioned other drugs may be low-molecular compounds, or high-molecular compounds such as proteins, polypeptides, polynucleotides (DNA, RNA, gene), antisense, decoy, antibody, or vaccine, etc. The dosage amount of the other drugs can be arbitrarily selected based on the clinically-used dosage. The formulating ratio of the therapeutic substance of the present invention and other drugs can be arbitrarily selected according to the age and the weight of those to be administered, administration method, administration time, target illness, symptom, combination, etc. For example, 0.01 to 100 parts by weight of other drugs may be used based on 1 part by weight of the therapeutic substance of the present invention. A combination of two or more types of other drugs at any ratio may be administered. Other drugs for the purpose of complementation and/or enhancement of the preventive and/or therapeutic effects of the therapeutic substance of the present invention include, based on the mechanism described above, not only drugs found until now, but also drugs to be found in the future.

The disease, on which the preventive and/or therapeutic effects are exerted by the companion drug, is not specifically limited, so far as it is a disease in which the prevention and/or treatment effects of the medicament of the present invention are supplemented and/or enhanced.

Other drugs for the purpose of complementation and/or enhancement of the preventive and/or therapeutic effects of the compounds of the present invention represented by formula (I) against allergic rhinitis include, for example, an antihistaminic agent, suppressor for mediator liberation, thromboxane synthetase inhibitor, antagonist for thromboxane A2 receptor, antagonist for leukotriene receptor, leukotriene synthase inhibitor, cytokine inhibitor, steroid agent, sympathomimetic agent, phosphadiesterase IV inhibitor, xanthine derivative, anticholinergic agent, anti-IgE antibody formulation, immunosuppressive agent, chemokine receptor antagonist, adhesion molecule inhibitor, other prostanoid receptor antagonist, nonsteroidal anti-inflammatory agent, nitric oxide synthase inhibitor, etc.

Other drugs for the purpose of complementation and/or enhancement of the preventive and/or therapeutic effects of the compound of the present invention represented by formula (I) against allergic conjunctivitis include, for example, an antihistaminic agent, suppressor for mediator liberation, thromboxane synthetase inhibitor, antagonist for thromboxane A2 receptor, antagonist for leukotriene receptor, leukotriene synthase inhibitor, cytokine inhibitor, steroid agent, sympathomimetic agent, phosphodiesterase IV inhibitor, xanthine derivative, anticholinergic agent, anti-IgE antibody formulation, immunosuppressive agent, chemokine receptor antagonist, adhesion molecule inhibitor, other prostanoid receptor antagonist, nonsteroidal anti-inflammatory agent, nitric oxide synthase inhibitor, etc.

Antihistaminic agents include, for example, ketotifen fumarate, mequitazine, azelastine hydrochloride, oxatomide, terfenadine, emedastine fumarate, epinastine hydrochloride, astemizole, ebastine, cetirizine hydrochloride, bepotastine, fexofenadine, loratadine, desloratadine, olopatadine hydrochloride, TAK-427, ZCR-2060, NIP-530, mometasone furoate, mizolastine, BP-294, andolast, auranofin, acrivastine, etc.

Suppressor for mediator liberation include, for example, tranilast, sodium cromoglycate, amlexanox, repirinast, ibudilast, tazanolast, pemirolast potassium, etc.

Thromboxane synthetase inhibitor include, for example, ozagrel hydrochloride, imitrodast sodium, etc.

Antagonist for thromboxane A2 receptor include, for example, seratrodast, ramatroban, domitroban calcium hydrate, KT-2-962, etc.

Antagonist for leukotriene receptor include, for example, pranlukast hydrate, montelukast, zafirlukast, MCC-847, KCA-757, CS-615, YM-158, L-740515, CP-195494, LM-1484, RS-635, A-93178, S-36496, BIIL-284, ONO-4057,etc.

Leukotriene synthase inhibitors include, for example, zyleuton, etc. Cytokine inhibitors include, for example, suplatast tosilate, etc.

Steroid agents include, for example, as an external medication, clobetasol propionate, diflorasone diacetate, fluocinonide, mometasone furoate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclometasone propionate, triamcinolone acetonide, flumetasone pivalate, alclometasone propionate, clobetasone butyrate, prednisolone, beclomethasone propionate, fludroxycortide, etc.

Internal remedies and injectable drugs include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butyl acetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone, etc.

Inhalation agents include beclomethasone propionate, fluticasone propionate, budesonide, flunisolide, triamcinolone, ST-126P, ciclesonide, dexamethasone palomithioate, mometasone furancarbonate, prasterone sulfonate, deflazacort, methylprednisolone suleptanate, methylprednisolone sodium succinate, etc.

Sympathomimetic agents include, for example, naphazoline nitrate, tetrahydrozoline hydrochloride, oxymetazoline hydrochloride, tramazoline hydrochloride, pseudoephedorine, salbutamol, salmeterol, formeterol, etc. Phosphodiesterase IV inhibitor include, for example, theophylline, cilomilast, roflumilast.

Xanthine derivatives include, for example, aminophylline, theophylline, doxophylline, cipamfylline, diprophylline.

Anticholinergic agents include, for example, ipratropium bromide, oxitropium bromide, flutropium bromide, cimetropium bromide, temiberin, tiotropium bromide, revatropate (UK-112166).

Anti-IgE antibody formulations include, for example, omalizamab. Immunosuppressive agent include, for example, protopic, ciclosporin.

Nonsteroidal anti-inflammatory drugs include, for example, sasapyrine, sodium salicylate, aspirin, aspirin dialuminate compounding, diflunisal, indomethacin, suprofen, ufenamate, dimethylisopropylazulene, bufexamac, felbinac, diclofenac, tolmetin sodium, clinoril, fenbufen, nabumetone, proglumetacin, indomethacin farnesyl, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, tiaprofen, oxaprozin, pranoprofen, loxoprofen sodium, aluminoprofen, zaltoprofen, mefenamic acid, aluminum mefenamate, tolfenamic acid, floctafenine, ketophenylbutazone, oxyphenbutazone, piroxicam, tenoxicam, ampiroxicam, Napageln ointment, epirizole, tiaramide hydrochloride, tinoridine hydrochloride, emorfazone, sulpyrine, migrenin, salicion, Sedes G, Amipylo-N, Solbon, pyrazolone-type remedy for common cold, acetaminophen, phenacetin, dimethothiazine mesylate, simetride-compounded agent, non-pyrazolone-type remedy for common cold.

The weight ratio of the compound represented by formula (I) to an other drug in combination is not specifically limited, Two or more other drugs may be arbitrarily administered in combination.

Other drugs for the purpose of complementation and/or enhancement of the preventive and/or therapeutic effects of the compound represented by formula (I) include, based on the mechanism described above, not only drugs found until now, but also drugs to be found in the future.

In order to use the compound represented by formula (I) or the non-toxic salts thereof according to the present invention, or the drug represented by formula (I) in combination with other drugs, for the above-mentioned purpose, they axe generally administered orally or parenterally, locally, or systemically.

The dosage may vary depending on the age, body weight, symptom, desired therapeutic effect, route of administration, duration, of treatment, etc. Generally, for a human adult, from 1 mg to 1000 mg per dose is orally administered once to several times per day, or from 1 mg to 100 mg is parenterally administered (preferably, via a nasal preparation, eye-drop, or ointment) once to several times per day, or continuously administered into vein for from 1 hour to 24 hours a day.

As the dosage may fluctuate according to various conditions as described above, a dose lower than the above-specified dose may in some instances be adequate, whereas a dose in excess of the above range may in some cases be required necessary.

In the course if administration of the compound represented by formula (I) or the non-toxic salt thereof, or the drug represented by formula (I) in combination with other drugs, for oral administration, they are used in a form of solid composition, liquid composition, or in other composition, and for parenterally administration, they are used in a form of an injection product, external product, suppository, etc.

Solid formulations for oral administration include a tablet, pill, capsule, powdered, drug, granule, etc.

Capsules include a hard capsule and soft capsule.

In such solid formulations, one or more active substances are blended with at least one inert diluent, for example, lactose, mannitol, glucose, hydroxypropyl cellulose, microcrystalline cellulose, starch, polyvinyl pyrrolidone, magnesium aluminometasilicate. The formulation may contain additives other than inert diluents, for example, a lubricant such as magnesium stearate, a disintegrant such as calcium carboxymethyl cellulose, a stabilizing agent such as lactose, a solubilizing agent such as glutamic acid or aspartic acid. If needed, the tablet or pill may be coated by a film made of gastric-soluble or enteric substances such as a white sugar, gelatin, hydroxypropyl cellulose, hydroxylpropylmethy cellulosephthalate, or may be coated by two or more layers. Additionally, capsules made of absorbable substances such as gelatin are also included.

Liquid formulations for oral administration include pharmaceutically acceptable opalizer, liquid solution, syrup, elixir, etc. In such liquid formulations, one or more active substances are included in a generally used inert diluent (for example, purified water, ethanol).

The formulations may contain, in addition to inert diluents, additives such as a wetting agent or suspension agent, a sweetening agent, a flavoring material, an aromatic substance, and a preservative.

Other formulations for oral administration include a spray which contains one or more active substances, and which is formulated by a publicly known method. The formulations may contain a stabilizing agent, such as sodium hydrogen sulfite and a buffering agent which provides isotonicity, and an isotonic agent such as sodium chloride, sodium citrate or citric acid. The method for producing a spray is described in, for example, U.S. Pat. Nos. 2,868,691 and 3,095,355 in detail.

The injectable formulations for parenteral administration according to the present invention include antibacterial aqueous and/or nonaqueous liquid solutions, suspensions and opalizers. The aqueous liquid solutions, and suspensions include, for example, distilled water for injection and normal saline. The nonaqueous liquid solutions and suspensions include, for example, propylene glycol, polyethyleneglycol, vegetable oils such as an olive oil, alcohols such as ethanol, Polysorbvate 80®, etc. Antibacterial aqueous and nonaqueous liquid solutions, suspensions and opalizers may be used as a mixture thereof. Such a formulation may further contain additives such as a preservative, wetting agent, emulsifier, dispersing agent, stabilizing agent (for example, lactose), solubilizing agent (for example, glutamic acid, aspartic acid). They are sterilized by filtration using a bacteria-retaining filter, by mixing with a bactericide, or by irradiation. They may be also used by preparing an sterile solid, formulation, for example, a freeze-dried product, and then prior to use, dissolve it into a sterilized or aseptic distilled water for injection or in other solvents.

Dosage forms of eye drop for parenteral administration include eye drops, suspension-type eye drops, emulsion-type eye drops, eye drops which are dissolved upon actual use, and eye ointment.

These eye drops can be manufactured according to known methods. For example, in the case of the eye drops, an isotonizing agent (sodium chloride, concentrated glycerol, etc.), a buffering agent (sodium phosphate, sodium acetate, etc.), a surfactant (Polysorbate 80 (trade name), polyoxyl stearate 40, polyoxyethylene hydrogenated castor oil, etc.), stabilizer (sodium citrate, sodium edentate, etc.), antiseptic agent (benzalkonium chloride, paraben, etc.), and the like are appropriately selected and prepared depending on the needs. They are sterilized in the final step or prepared by an sterile operation.

Inhalation formulations for parenteral administration include aerosol, preparation, powder for inhalation, or liquid for inhalation. The liquid for inhalation may be in such a form that, the ingredient is dissolved or suspended in water or in other appropriate media in actual use.

Those inhalation formulations are prepared according to known methods.

For example, in the case of liquid for inhalation, an antiseptic agent (benzalkonium chloride, paraben, etc.), coloring agent, buffer (sodium phosphate, sodium acetate, etc.), isotonizing agent (sodium chloride, concentrated glycerol, etc.), thickener (carboxyvinyl polymer, etc.), absorption promoter, etc., are appropriately selected and prepared depending on needs.

In the case of powder for inhalation, a lubricant (stearic acid, salt thereof, etc.), binder (starch, dextrin, etc.), excipient (lactose, cellulose, etc.), coloring agent, antiseptic (benzalkonium chloride, paraben, etc.), absorption promoter, etc., are appropriately selected and prepared according to need.

In the administration of the liquid for inhalation, a spraying device (atomizer, nebulizer, etc.) is commonly used and in the administration of the powder for inhalation, an administering device for inhalation of powdery pharmaceutical is commonly used.

Other compositions for parenteral administration include an external application, ointment, liniment, and suppository for intrarectal administration, and pessary for intravaginal administration etc., containing one or more active compound(s) which can be prepared by known methods.

EXAMPLES

The following examples and biological examples illustrate the present invention in detail, but do not limit the present invention.

The solvents in the parentheses show the elating or developing solvents, and the ratios of the solvents used are by volume in chromatographic separations or TLC. The solvents in the parentheses in NMR show the solvents for measurement.

The compound names represented in the examples were named using ACD/Name (Version 6.00, Advanced Chemistry Development Inc.).

Example 1

Methyl (3-nitro-4-(trifluoromethyl)phenyl) acetate

Under an argon atmosphere, 3-nitro-4-trifluoromethyl) benzoic acid (12 g) was dissolved in 1,2-dimethoxyethane (120 mL). Oxalyl chloride (10.4 mL) and anhydrous N,N-dimethylformamine (one drop) were added to the reaction mixture, and the mixture was stirred for 30 minutes at 40° C. The reaction mixture was concentrated to obtain a acid chloride.

To a solution (2.0 M, 29.8 mL) of trimethylsilyldiazomethane in n-hexane and a solution of triethylamine (16.6 mL) in tetrahydrofuran (60 mL), a solution of the previous acid chloride in tetrahydrofuran (60 mL) was dropped and was stirred for 1 hour at room temperature. The reaction mixture was diluted with ethyl acetate and the organic layer was washed with water and saturated brine solution and was dried by anhydrous magnesium sulphate. A diazoketone was obtained by removing the solvent.

To a solution (120 mL) of the diazoketone and triethylamine (7.5 mL) in ethanol, silver acetate (5.0 g) was added at 60° C. and stirred for 30 minutes. After the reaction mixture was cooled to room temperature, ethyl acetate and water were added thereto, which was filtered with Celite (trade name). The organic layer that was separated from the filtrate was washed with water and saturated brine solution, and was dried by anhydrous magnesium sulphate. The title compound (8.6 g) having the following physical data was obtained by purifying the residue obtained by removing the solvent with silica gel column chromatography (n-hexane:ethyl acetate=4:1).

TLC: Rf 0.54 (n-hexane:ethyl acetate=1:2).
$^1$H-NMR: (CDCl$_3$) δ 3.74, 3.77, 7.64, 7.78, 7.82.

Example 2

Methyl 1-(3-nitro-4-(trifluoromethyl)phenyl)cyclopropanecarboxylate

Under an argon atmosphere, the compound (8.4 g) synthesized in Example 1 and 1,2-dibromoethane (13.7 mL) were dissolved in N-methylpyrrolidone (150 mL). 60% sodium hydride (2.8 g) was added thereto during ice-cooling, and stirred for 1 hour at room temperature. The reaction mixture was diluted with water and was extracted with ethyl acetate. The organic layer was washed with water and saturated brine solution, and was dried with anhydrous magnesium sulphate. The title compound (5.1 g) having the following physical data was obtained by purifying the residue obtained by removing the solvent with silica gel column chromatography (n-hexane: ethyl acetate=4:1).

TLC: Rf 0.56 (n-hexane:ethyl acetate=1:2).
$^1$H-NMR: (CDCl$_3$) δ 1.23, 1.78, 3.64, 7.68, 7.78, 7.88.

Example 3

Methyl 1-(3-amino-4-(trifluoromethyl)phenyl)cyclopropanecarboxylate

An aqueous solution (22.5 mL-22.5 mL) of the compound synthesized in Example 2 (5.1 g) and iron (3.9 g) in acetic acid were stirred at 60° C. for 1 hour. The reaction mixture was diluted with ethyl acetate and filtrated with Celite (trade name). The filtrate was washed with saturated sodium bicarbonate water, water, and saturated brine solution, and was dried with anhydrous magnesium sulphate. The title compound (3.9 g) having the following physical data was obtained by allowing the residue obtained by removing the solvent to recrystallize from a mixed solvent of n-hexane and ethyl acetate.

TLC:Rf 0.55 (n-hexane: ethyl acetate:acetic acid=1:2);
$^1$H-NMR: (CDCl$_3$) δ 1.18, 1.59, 3.62, 4.13, 6.72, 6.75, 7.34

Example 4

(2-fluorophenyl)methylamine

Under an argon gas atmosphere, formic acid (6.1 mL) was added dropwise in acetic anhydride (15.5 mL) at 0° C., which was stirred for 2 hours at 50° C. After being cooled to room temperature, the reaction mixture was diluted with tetrahydrofuran (THF; 10 mL). To the diluent, a solution of 2-fluoroaniline (5.56 g) in THF (20 mL) was added at room temperature and the mixture was stirred for 1 hour at room temperature. The reaction mixture was concentrated. The obtained residue was then dissolved in anhydrous THF (25 mL). Under an argon atmosphere, to the solution of the residue in anhydrous THF (25 mL), borane tetrahydrofuran complex (1M THF solution; 125 mL) was added at 0° C. and the mixture was stirred for 2 hours at 50° C. After the reaction mixture was cooled to room temperature, methanol (30 mL) and 4N hydrogen chloride dioxane solution (10 ml) were added on an ice bath and the mixture was stirred for 1 hour at 60° C. The concentrated reaction mixture was added to 2N sodium hydroxide solution, and was extracted with ethyl acetate. The organic layer was washed with saturated brine solution and was dried by anhydrous sodium sulfate. The solution was filtered with Celite (trade name) and the filtrate was concentrated. To the residue, the mixed solvent (hexane:ethyl acetate=10:1) was added and was filtered on silica-gel. The title compound (6.45 g) having the following physical data was obtained by concentrating the effluent.

Example 5

(2S)-3-((2-fluorophenyl)(methyl)amino)-1,2-propanediol

Under an argon atmosphere, a mixture of the compound (1.24 g) prepared in Example 4, (R)-(+)-glycidol (1.11 g, Aldrich, 98% ee), and ethanol (1 mL) was stirred for 12 hours at 50° C. The title compound having the following physical data was obtained by concentrating the reaction mixture. The obtained title compound was used for the following reaction without purification.

TLC:Rf 0.40 (n-hexane:ethyl acetate=1:1).

Example 6

((2S)-4-methyl-3,4-dihydro-2H-1,4-benzoxazin-2-yl)methanol

To a solution of the compound prepared in Example 5 in anhydrous dimethylformamide (DMF; 10 mL), potassium t-butoxide (1.68 g) was added on water bath, and the mixture was stirred for 3 hours at 80° C. The reaction mixture was added to water, which was extracted with ethyl acetate. The organic layer was washed with saturated brine solution and was dried with anhydrous sodium sulfate. The solution was filtered with Celite (trade name) and the filtrate was concentrated. The title compound (1.55 g, 97.6% ee) having the following physical data was obtained by purifying the residue with silica gel column chromatography (hexane:ethyl acetate=3:1).

TLC:Rf 0.35 (n-hexane:ethyl acetate=2:1).
The optical purity of the title compound was determined by using high performance liquid chromatography (HPLC).
Column: CHIRALCEL OD (Daicel Chemical Industries, Ltd.), 0.46 cm φ×25 cm
Flow rate: 1 mL/minute Solvent: hexane: 2-propanol=93:7
Detection wave-length: 254 nm
Retention time: 30.70 minutes
Temperature: 24° C.

Example 7

((2S)-4-methyl-3,4-dihydro-2H-1,4-benzoxazin-2-yl)methyl 4-methylbenzenesulfonate Under an argon atmosphere, to a solution of the compound (3.06 g) prepared in Example 6 in tetrahydrofuran (9 mL), triethylamine (5 mL) was added. To the reaction solution, a solution of p-toluensulfonic acid chloride (3.42 g) in tetrahydrofuran (9 mL) and N,N-dimethylaminopyridine (209 mg) were added and the mixture was stirred for 4 hours at room temperature. After adding water, the reaction solution was extracted with methyltert-butyl ether. The extract was solidified by adding isopropyl-alcohol to the residue obtained by concentrating the organic layer. The title compound (5.12 g) having the following physical data was obtained by washing the filtered solid with isopropyl alcohol and drying.

TLC:Rf 0.81 n-hexane:ethyl acetate=1:1).

Example 8

(2S) -2-((4-bromo-3,5-dimethylphenoxy)methyl)-4-methyl-3,4-dihydro-2H-1,4-benzoxazine Under an argon atmosphere, to a solution of 4-bromo-3,5-dimethylphenol (150 g) in anhydrous N,N-dimethylacetamide (1 L), potassium carbonate (206 g) and the compound prepared in Example 7 (249 g) were added in sequence. The reaction mixture was stirred for 7 hours at 100° C. After the reaction mixture was cooled to room temperature, water was added thereto and was extracted with ethyl acetate. The organic layer was washed with water and saturated brine solution, and was dried by anhydrous magnesium sulphate. The residue obtained by removing the solvent was allowed to recrystallize from n-hexane. The title compound (244 g) having the following physical data was obtained by filtering it, TLC:Rf 0.41 (n-hexane:ethyl acetate=2:1);

$^1$H-NMR: (CDCl$_3$) δ 2.31, 2.82, 3.14, 3.34, 4.13, 4.49-4.59, 6.53-6.63, 6.67-6.74, 6.74-6.83, 6.86.

Example 9

2,6-dimethyl-4-(((2S) -4-methyl-3,4-dihydro-2H-1,4-benzoxazin-2-yl)methoxy)benzoic acid Under an argon atmosphere, the compound (219 g) prepared in Example 8 was dissolved in anhydrous tetrahydrofuran (1.7 L) and stirred at −78° C. n-butyl lithium (1.58 M n-hexane solution, 421 mL) was added to the solution and was stirred for 1 hour. After carbon dioxide was blown into the solution, the solution was stirred for 2 hours while heating up to 0° C. After the residue obtained by removing the solvent was diluted with 1N sodium hydroxide aqueous solution, the solution was washed by tert-butylmethylether. A 5N hydrochloric acid was added to the aqueous phase while stirring to obtain a crystal. The title compound (183 g) having the following physical data was obtained by filtrating and drying the crystal.

TLC:Rf 0.25 (chloroform:methanol=9:1);

$^1$H-NMR: (CDCl$_3$) δ 2.25, 2.82, 3.15, 3.34, 4.16, 4.47-4.62, 6.54-6.64, 6.67-6.84, 12.86.

Example 10

2,6-dimethyl-4-(((2S)-4-methyl-3,4-dihydro-2H-1,4-benzoxazin-2-yl)methoxy)benzoyl chloride Under an argon atmosphere, the compound (0.97 g) prepared in Example 9 was dissolved in 1,2-dimethoxyethane (6 mL). Oxalyl chloride (0.26 mL) and anhydrous N,N-dimethylformamide (one drop) were added to the reaction mixture, and was stirred for 30 minutes at 40° C. The reaction mixture was concentrated to obtain the title compound.

Example 11

Methyl 1-(3-((2,6-dimethyl-4-(((2S)-4-methyl-3,4-dihydro-2H-1,4-benzoxazin-2-yl)methoxy)benzoyl)amino-4-(trifluoromethyl)phenyl)cyclopropanecarboxylate To the solution of the compound synthesized in Example 3 (1.0 g) in acetonitrile (2.5 mL) and pyridine (1.2 mL), the solution of the compound synthesized in Example 10 in acetonitrile (2.5 mL) was added dropwise and stirred over night at 50° C. The reaction mixture was diluted with ethyl acetate and the organic layer was washed with a 1N hydrochloric acid, water and saturated brine solution and was dried with anhydrous magnesium sulphate. The title compound (0.50 g) having the following physical data was obtained by purifying the residue obtained by removing the solvent by silica gel column chromatography (n-hexane:ethyl acetate=4:1).

TLC:Rf 0.51 (n-hexane:ethyl acetate:acetic acid=1:2);

$^1$H-NMR: (CDCl$_3$) δ 1.30, 1.68, 2.38, 2.92, 3.22, 3.39, 3.64, 4.10, 4.22, 4.62, 6.63, 6.82, 7.28, 7.50, 7.58, 8.38.

Example 12

1-(3-((2,6-dimethyl-4-(((2S)-4-methyl-3,4-dihydro-2H-1,4-benzoxazin-2-yl)methoxy)benzoyl)amino)-4-(trifluoromethyl)phenyl)cyclopropanecarboxylic acid

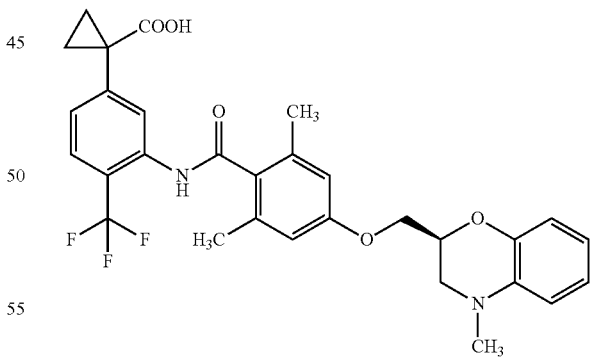

To the mixture of the compound synthesized in Example 11 (0.50 g), tetrahydrofuran (1 mL), and methanol (1mL), 1N aqueous sodium hydroxide (1 mL) was added and stirred for 2 hours at room temperature. After the reaction mixture was neutralized by addition of a 1N hydrochloric acid (1 mL), water was added thereto and extracted, with ethyl acetate. The organic layer was washed with saturated brine solution and was dried with anhydrous magnesium sulphate. The title compound (0.41 g) of the present invention having the following physical data was obtained by purifying the residue obtained by removing the solvent with silica gel column chromatography (methylene chloride:ethyl acetate=20:1).

TLC:Rf 0.63 (chloroform:methanol=10:1);

$^1$H-NMR: (DMSO-D6) δ 1.21, 1.52, 2.31, 2.83, 3.16, 3.37, 4.17, 4.55, 6.58, 6.75, 7.44, 7.68, 9.96, 12.54.

Example 13

4-bromo-3-ethylphenol

Under argon atmosphere, to the mixture of 3-ethylphenol (11.2 g), methylene chloride (30 mL), and methanol (20 mL), tetra-n-butylammonium tribromide (24.9 g) was added and stirred for 1 hour at room temperature. The reaction mixture was diluted with ethyl acetate and the organic layer was washed with a 1N hydrochloric acid, water and saturated brine solution and was dried by anhydrous magnesium sulphate. The title compound (11.2 g) having the following physical data was obtained by removing the solvent.

TLC:Rf 0.49 (n-hexane:ethyl acetate:acetic acid=1:4);

$^1$H-NMR: (CDCl$_3$) δ 1.22, 2.69, 4.92, 6.57, 6.74, 7.37.

Example 14

(2S)-2-(4-bromo-3-ethylphenoxy)methyl-4-methyl-3,4-dihydro-2H-1,4-benzoxazine

Under an argon atmosphere, to the mixture of the compound synthesized in Example 13 (11.2 g), the compound synthesized in Example 7 (16.9 g), and N,N-dimethylformamide (50 mL), cesium chloride (18.2 g) was added and stirred overnight at 70° C. The reaction mixture was diluted with ethyl acetate and the organic layer was washed with a 1N hydrochloric acid, water and saturated brine solution, and was dried with anhydrous magnesium sulphate. The title compound (17.0 g) having the following physical data was obtained by purifying the residue obtained by removing the solvent with silica gel column chromatography (n-hexane:ethyl acetate=6:1).

TLC:Rf 0.49 (n-hexane-ethyl acetate:acetic acid=1:6);

$^1$H-NMR: (CDCl$_3$) δ 1.22, 2.69, 2.91, 3.23, 3.38, 4.09, 4.18, 4.61, 6.63, 6.82, 7.39.

Example 15

2-ethyl-4-(((2S-4-methyl-3,4-dihydro-2H-1,4-benzoxazin-2-yl)methoxy)benzoic acid Under an argon atmosphere, to the mixture of the compound synthesized in Example 14 (17.0 g) and tetrahydrofuran (113 mL), a solution of n-butyl lithium in n-hexane (1.6 M, 32.3 mL) was added at −78° C. and stirred for 1 hour. Carbon dioxide was blown into the reaction mixture at −78° C., and the reaction mixture was stirred for 30 minutes. The reaction mixture was diluted with ethyl acetate and the organic layer was washed with a 1N hydrochloric acid, water and saturated brine solution, and was dried with anhydrous magnesium sulphate. The title compound (9.5 g) having the following physical data was obtained by allowing the residue obtained by removing the solvent to recrystallize from a mixed solvent of n-hexane and ethyl acetate.

TLC:Rf 0.63 (chloroform:methanol=10:1);

$^1$-NMR: (DMSO-D6) δ 1.16, 2.81, 2.92, 3.17, 3.37, 4.22, 4.57, 6.59, 6.70, 6.85, 7.80.

Example 16

Methyl 1-(3-((2-ethyl-4-(((2S)-4-methyl-3,4-dihydro-2H-1,4-benzoxazin-2-yl)methoxy)benzoyl)amino)-4-(trifluoromethyl)phenyl)cyclopropanecarboxylate The title compound (700 mg) having the following physical data was obtained by the similar method as Examples 10 and 11, using the compounds prepared in Example 15 (971 mg) and the compound prepared in Example 2 (1000 mg).

TLC:Rf 0.47 (n-hexane:ethyl acetate:acetic acid=1:2);

$^1$H-NMR: (CDCl$_3$) δ 1.23, 1.64, 2.90, 3.24, 3.40, 3.63, 4.18, 4.24, 4.63, 6.68, 6.84, 7.23, 7.42, 7.58, 7.76, 8.37.

Example 17

1-(3-((2-ethyl-4-(((2S)-4-methyl-3,4-dihydro-2H-1,4-benzoxazin-2-yl)methoxy)benzoyl)amino)-4-(trifluoromethyl)phenyl)cyclopropanecarboxylic acid

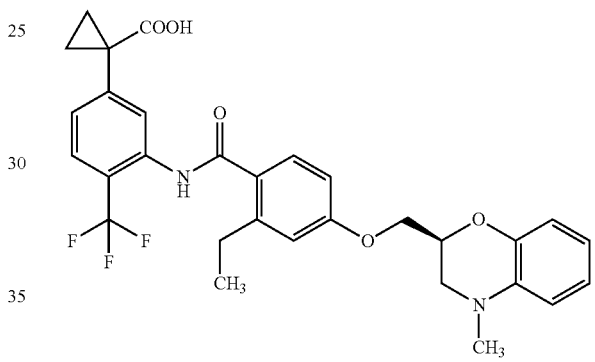

The compound of the present invention (366 mg) having the following physical data was obtained from the compound prepared in Example 16 (700 mg) by the similar method as Example 12.

TLC:Rf 0.63 (chloroform:methanol=1:10);

$^1$H-NMR: (CDCl$_3$) δ 1.16, 1.17, 1.50, 2.77, 2.84, 3.18, 3.38, 4.23, 4.58, 6.60, 6.71, 6.92, 7.47, 7.69, 9.88, 12.56.

Example 18

2-ethyl-6-methyl-4-(((2S)-4-methyl-3,4-dihydro-2H-1,4-benzoxazin-2-yl)methoxy)benzoic acid Under an argon atmosphere, the compound prepared in Example 9 (100 g) was dissolved in anhydrous THF (1 L) and stirred at −20° C. Methyl lithium (3M diethoxymethane solution, 255 mL) was added to the solution. The reaction mixture was heated to 40° C. and stirred for 1 hour, followed by cooling to 0° C. Methyl iodide (57 mL) was added dropwise in the mixture, followed by heating to room temperature and stirring for 30 minutes. 2N aqueous sodium hydroxide was added to the mixture and the solvent was removed to obtain a residue. To the residue, 5N hydrochloric acid (270 mL) was added, and extracted with ethyl acetate. The organic layer was washed with water and saturated brine solution, and was dried with anhydrous magnesium sulphate. The residue obtained by removing the solvent was allowed to recrystallize from n-hexane. The title compound (80 g) having the following physical data was obtained by filtering it.

TLC:Rf 0.66 (chloroform:methanol=5:1);

¹H-NMR: (CDCl₃) δ 1.13, 2.25, 2.57, 2.82, 3.15, 3.34, 4.16, 4.47-4.62, 6.52-6.64, 6.66-6.74, 6.74-6.83, 12.87.

Example 19

2-ethyl-6-methyl-4-(((2S)-4-methyl-3,4-dihydro-2H-1,4-benzoxazin-2-yl)methoxy)benzoyl chloride Under an argon atmosphere, the compound prepared in Example 18 (79 g) was dissolved in 1,2-dimethoxyethane (500 mL). The reaction mixture was added with anhydrous N,N-dimethylformamide (3 drops) and oxalyl chloride (24 mL), and stirred at 40° C. for an hour. The reaction mixture was concentrated to obtain the title compound.

Example 20

Methyl 1-(3-((2-ethyl-6-methyl-4-(((2S)-4-methyl-3,4-dihydro-2H-1,4-benzoxazine-2-yl)methoxy)benzoyl)amino-4-(trifluoromethyl)phenyl) cyclopropanecarboxylate To a solution of the compound synthesized in Example 3 (60 g) in acetonitrile (400 mL), pyridine (94 mL), and then a solution of the compound prepared in Example 19 in acetonitrile (200 mL) were added. The reaction mixture was stirred at 40° C. overnight. To the reaction mixture methanol (100 mL) was added, and stirred for 30 minutes.

The mixture was extracted with a mixed solvent of ethyl acetate/n-hexane, and the organic layer was washed with 1N hydrochloric acid, saturated sodium bicarbonate water, water, and saturated saline. After drying with anhydrous magnesium sulphate, the title compound (87 g) having the following physical data was obtained by purifying the residue resulting from removing the solvent by silica gel column chromatography (n-hexane:ethyl acetate=3:1).

TLC:Rf 0.40 (n-hexane:ethyl acetate=3:2);
¹H-NMR: (CDCl₃) δ 1.26, 1.29-1.34, 1.66-1.73, 2.37, 2.70, 2.91, 3.26, 3.40, 3.67, 4.12, 4.25, 4.59-4.71, 6.63-6.75, 6.81-6.93, 7.25-7.31, 7.53, 7.58, 8.40.

Example 21

1-(3-((2-ethyl-6-methyl-4-(((2S)-4-methyl-3,4-dihydro-2H-1,4-benzoxazin-2-yl)methoxy)benzoyl)amino)-4-(trifluoromethyl)phenyl)cyclopropanecarboxylic acid

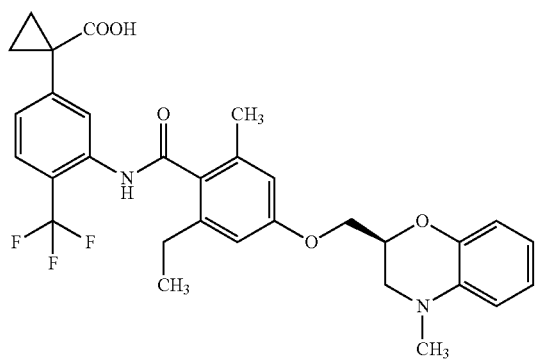 [SMILES: CCc1cc(OC[C@@H]2CN(C)c3ccccc3O2)cc(C)c1C(=O)Nc1cc(C2(C(=O)O)CC2)ccc1C(F)(F)F]

The mixture of the compound prepared in Example 20 (87 g) and methanol (870 mL) was added with 1N aqueous sodium hydroxide (150 mL) and stirred at 60° C. for 6 hours. The solvent was removed and the residue was dilluted with water. After washing with methyl tert-butylmethyl ether, the solution was neutralized by the addition of 5N hydrochloric acid. The solution was extracted with ethyl acetate, and the organic layer was washed with water and saturated brine solution, and then dried with anhydrous magnesium sulphate. The compound of the present invention (79.6 g) having the following physical data was obtained by allowing the residue resulting from removing the solvent to recrystallize from a mixed solvent of methanol and water.

TLC:Rf 0.41 (chloroform:methanol=9:1);
¹H-NMR: (DMSO-d₆) δ 1.13-1.25, 1.49-1.57, 2.33, 2.63, 2.84, 3.17, 3.37, 4.19, 4.51-4.62, 6.55-6.55, 6.68-6.86, 7.40-7.52, 7.69, 9.99, 12.59.

Example 22

Methyl (3-amino-4-(trifluoromethyl)phenyl)acetate

An aqueous solution (9 mL- 1 mL) of the compound synthesized in Example 1 (1.9 g) and iron (1.6 g) in acetic acid was stirred at 70° C. for 2 hours. The reaction mixture was diluted with ethyl acetate and filtrated with Celite (trade name). The filtrate was washed with saturated sodium bicarbonate water, water, and saturated brine solution and was dried with anhydrous magnesium sulphate. The title compound (1.3 g) having the following physical data was obtained by purifying the residue resulting from removing the solvent by silica gel column chromatography (n-hexane:ethyl acetate-5:1).

TLC:Rf 0.44 (n-hexane:ethyl acetate:acetic acid=1:1);
¹H-NMR: (CDCl₃) δ 3.55, 3.70, 4.16, 6.69, 7.37.

Example 23

Methyl (3-((2,6-dimethyl-4-(((2S)-4-methyl-3,4-dihydro-2H-1,4-benzoxazin-2-yl)methoxy)benzoyl)amino)-4-(trifluoromethyl)phenyl)acetate The compound synthesized in Example 22 (0.57 g) was dissolved in acetonitrile (2.5 mL) and pyridine (0.37 mL), a solution of the compound synthesized in Example 10 (0.75 g) in acetonitrile (2.5 mL) was added dropwise thereto, and then stirred overnight at 50° C. The reaction mixture was diluted with ethyl acetate and the organic layer was washed with 1N hydrochloric acid, water and saturated brine solution, and was dried with anhydrous magnesium sulphate. The title compound (0.35 g) having the following physical data was obtained by purifying the residue resulted from removing the solvent by silica gel column chromatography (n-hexane:ethyl acetate=4:1).

TLC:Rf 0.54 (n-hexane: ethyl acetate:acetic acid=1:1);
¹H-NMR: (CDCl₃) δ 2.39, 2.91, 2.92, 3.24, 3.39, 3.77, 4.17, 4.22, 4.63, 6.68, 6.83, 7.21, 7.53, 7.60, 8.38.

Example 24

(3-((2,6-dimethyl-4-(((2S)-4-methyl-3,4-dihydro-2H-1,4-benzoxazin-2-yl)methoxy)benzoyl)amino)-4-(trifluoromethyl)phenyl)acetic acid

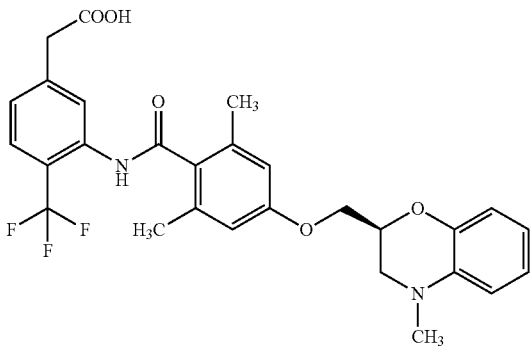 [SMILES: Cc1cc(OC[C@@H]2CN(C)c3ccccc3O2)cc(C)c1C(=O)Nc1cc(CC(=O)O)ccc1C(F)(F)F]

To the mixture of the compound synthesized in Example 23 (0.35 g), tetrahydrofuran (2 mL) and methanol (2 mL), 1N aqueous sodium hydroxide (2 mL) was added, and stirred for 2 hours at room temperature. After the reaction mixture was neutralized by the addition of 1N hydrochloric acid (2 mL), water was added and extracted with ethyl acetate. The organic layer was washed with saturated brine solution and was dried with anhydrous magnesium sulphate. The compound of the present invention (0.28 g) having the following physical data was obtained by allowing the residue resulted from removing the solvent to recrystallize from a mixed solvent of n-hexane and ethyl acetate.

TLC:Rf 0.49 (chloroform:methanol=9:1);
$^1$H NMR: (DMSO-D6) δ 2.31, 2.83, 3.16, 3.36, 3.74, 4.17, 4.56, 6.59, 6.75, 7.38, 7.46, 7.70, 9.96.

Example 25

Methyl (3-((2-ethyl-6-methyl-4-(((2S)-4-methyl-3,4-dihydro-2H-1,4-benzoxazin-2-yl)methoxy)benzoyl)amino)-4-(trifluoromethyl)phenyl)acetate The title compound (40 g) having the following physical data was obtained by the same method as Examples 19 and 20, using the compound prepared in Example 19 (3 9g) and the compound prepared in Example 22 (36 g).

TLC:Rf 0.64 (n-hexane:ethyl acetate:acetic acid=1:2);
$^1$H-NMR: (CDCl$_3$) δ 1.24, 2.38, 2.67, 2.92, 3.24, 3.41, 3.78, 4.12, 4.23, 4.62, 6.70, 6.83, 7.22, 7.54, 7.60, 8.38.

Example 26

(3-((2-ethyl-6-methyl-4-(((2S)-4-methyl-3,4-dihydro-2H-14-benzoxazin-2-yl)methoxy)benzoyl)amino)-4-(trifluoromethyl)phenyl)acetic acid

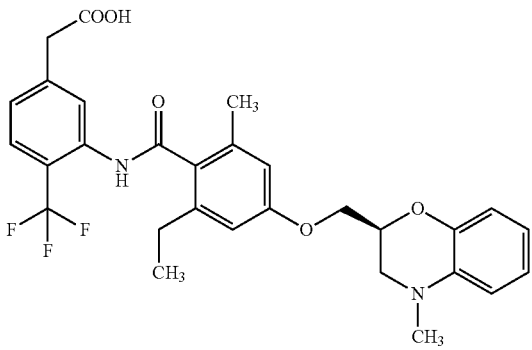 [SMILES: CCc1cc(OC[C@@H]2CN(C)c3ccccc3O2)cc(C)c1C(=O)Nc1cc(CC(=O)O)ccc1C(F)(F)F]

The title compound (31 g) having the following physical data was obtained by the same method as Example 21, using the compound prepared in Example 25 (40 g).

TLC:Rf 0.39 (chloroform:methanol=9:1);
$^1$H-NMR: (DMSO-D6) δ 1.19, 2.33, 2.63, 2.83, 3.17, 3.37, 3.75, 4.19, 4.56, 6.60, 6.75, 7.38, 7.45, 7.70, 9.98.

Example 27

Methyl hydroxy(3-((2,6-dimethyl-4-(((2S)-4-methyl-3,4-dihydro-2H-1,4-benzoxazin-2-yl)methoxy)benzoyl)amino)-4-(trifluoromethyl)phenyl)acetate Under an argon atmosphere, to the mixture of the compound synthesized in Example 23 (205 mg) and tetrahydrofuran (2 mL), a solution of sodium bis(trimethylsilyl)amide in tetrahydrofuran (1.0 M, 1.1 mL) was added at −78° C., and stirred for an hour at the same temperature. The reaction mixture was added with a solution of (2S, 8AR)-(−)-(camphorsulfonyl)oxaziridine (250 mg) in tetrahydrofuran (2 mL) at −78° C., and stirred at 0° C. for 30 minutes. The reaction mixture was diluted with ethyl acetate. The organic layer was washed with 1N hydrochloric acid, water, and saturated brine solution, then dried with anhydrous magnesium sulphate. The title compound (180 mg) having the following physical data was obtained by purifying the residue obtained by removing the solvent by silica gel column chromatography (n-hexane:ethyl acetate=1:1).

TLC:Rf 0.37 (n-hexane:ethyl acetate=1:1);
$^1$H -NMR: (CDCl$_3$) δ 2.39, 2.91, 3.23, 3.39, 3.61, 3.82, 4.11, 4.23, 4.62, 5.30, 6.63, 6.69, 6.82, 7.38, 7.56, 7.63, 8.55.

Example 28

Hydroxy(3-((2,6-dimethyl-4-(((2S)-4-methyl-3,4-dihydro-2H-1,4-benzoxazin-2-yl)methoxy)benzoyl)amino)-4-(trifluoromethyl)phenyl)acetic acid

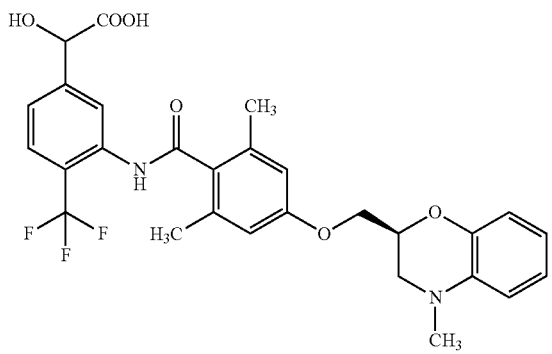 [SMILES: Cc1cc(OC[C@@H]2CN(C)c3ccccc3O2)cc(C)c1C(=O)Nc1cc(C(O)C(=O)O)ccc1C(F)(F)F]

The mixture of the compound synthesized in Example 27 (180 mg), tetrahydrofuran (2 mL) and methanol (2 mL) was added with an 1N aqueous solution (2 mL) of sodium hydroxide, and stirred for ten minutes at room temperature. The reaction mixture was neutralized by the addition of 1N hydrochloric acid (2 mL), added with water, and extracted with ethyl acetate. The organic layer was washed with saturated brine solution and was dried with anhydrous magnesium sulphate. The compound of the present invention (90 mg) having the following physical data was obtained by removing the solvent.

TLC:Rf 0.50 (chloroform:methanol:water=40:20:1);
$^1$H-NMR: (DMSO-D6) δ 2.32, 2.83, 3.16, 3.36, 4.17, 4.55, 5.17, 6.58, 6.77, 7.52, 7.61, 7.75, 9.99.

Example 29

Methyl 2-(3-((2,6-dimethyl-4-(((2S)-4-methyl-3,4-dihydro-2H-1,4-benzoxazin-2-yl)methoxy)benzoyl)amino)-4-(trifluoromethyl)phenyl)propionate Under argon atmosphere, to the mixture of the compound synthesized in Example 23 (330 mg) and tetrahydrofuran (3 mL), a solution of lithium diisopropylamide in heptane-tetrahydrofuran-ethylbenzene (2.0 M, 0.67 mL) was added at −78° C. and stirred at the same temperature for two hours. The reaction mixture was added with methyl iodide (259 mg) at −78° C. and stirred at −20° C. for 2 hours. The reaction mixture was diluted with ethyl acetate. The organic layer was washed with 1N hydrochloric acid, water and saturated brine solution, then dried with anhydrous magnesium sulphate. The title compound (170 mg) having the following physical data was obtained by purifying the residue resulted from removing the solvent by silica gel column chromatography (n-hexane: ethyl acetate=3:1).

TLC:Rf 0.52 (n-hexane:ethyl acetate:acetic acid=1:2);
$^1$H-NMR: (CDCl$_3$) δ 1.60, 2.39, 2.92, 3.24, 3.39, 3.62, 8.83, 4.13, 4.22, 4.62, 6.62, 6.70, 6.83, 7.22, 7.53, 7.59, 8.38.

Example 30

Methyl 2-hydroxy-2-(3-((2,6-dimethyl-4-(((2S)-4-methyl-3,4-dihydro-2H-1,4-benzoxazin-2-yl)methoxy)benzoyl)amino)-4-(trifluoromethyl)phenyl)propionate The title compound (600 mg) having the following physical data was obtained by the same method as Example 27, using the compounds prepared in Example 29 (800 mg).

TLC:Rf 0.47 (n-hexane:ethyl acetate:acetic acid=1:1);
$^1$H-NMR: (CDCl$_3$) δ 1.84, 2.38, 2.91, 3.25, 3.39, 3.86, 3.90, 4.13, 4.23, 4.63, 6.66, 6.71, 6.86, 7.51, 7.63, 8.64.

Example 31

2-hydroxy-2-(3-((2,6-dimethyl-4-(((2S)-4-methyl-3,4-d hydro-2H-1,4-benzoxazin-2-yl) methoxy)benzoyl)amino)-4-(trifluoromethyl)phenyl)propionic acid

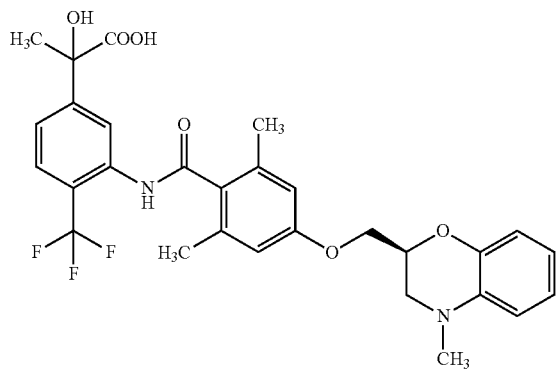 [SMILES: Cc1cc(OC[C@@H]2CN(C)c3ccccc3O2)cc(C)c1C(=O)Nc1cc(C(C)(O)C(=O)O)ccc1C(F)(F)F]

The title compound (380 mg) having the following physical data was obtained by the same method as Example 28, using the compounds prepared in Example 30 (600 mg).

TLC:Rf TLC:Rf 0.29 (chloroform:methanol=5:1);
$^1$H-NMR: (DMSO-D6) δ 1.63, 2.32, 2.83, 3.16, 3.38, 4.18, 4.57, 6.60, 6.77, 7.61, 7.71, 7.74, 9.99.

The biological examples below demonstrate that the compound of the present invention represented by formula (I) has a significant DP receptor antagonistic activity, does not strongly inhibit the drug-metabolizing enzyme, and is highly selective against other DP receptors.

Biological Example 1

Measurement of DP Receptor Antagonistic Activity Using Human Platelet-Rich Plasma (PRP)

Blood was collected from the cubital vein of a healthy adult who gave written informed, consent, using a syringe filled with a 3.8% sodium citrate solution of about one ninth of predetermined volume. The collected blood was subjected to centrifugal separation at 100 G, at room temperature for 15 minutes to obtain PRP in the upper layer. EDTA was added to the obtained PRP so that the final concentration thereof to be about 10 mmol/L. The PRP was subjected to centrifugal separation at 1500 G, at room temperature for 15 minutes to obtain supernatant platelet poor plasma (PPP). After the obtained platelet pellets were suspended, the suspension was diluted with PPP so that the platelet density to be adjusted to $5.0 \times 10^5/\mu L$. To the obtained platelet suspension, 3-isobutyl-1-methylxanthine and prostanoid EP3 receptor antagonist were added so that the final concentrations thereof to be 8 mmol/L and 1 μmol/L, respectively.

297 μL of the prepared PRP was dispensed to each test tube, followed by subjecting to incubation at 37° C. for 5 minutes. After adding 1.5 μL of DMSO or a variety of concentrations of the compound of the present invention, 10 minutes of incubation was carried out at 37° C. 1.5 μL of DMSO or PGD2 (final concentration: 3 μmol/L) was added thereto to initiate the reaction. After 15 minutes of incubation was carried out at 37° C., 300 μmol/L of ice-cooled 10% trichloroacetic acid (TCA) was added thereto to terminate the reaction. The TCA-treated sample was subjected to centrifugal separation at 15,000 G for 3 minutes at 4° C. The concentration of thus obtained supernatant cAMP was measured by enzyme immunoassay using cAMP EIA system. (Amersham plc). 300 μL of the supernatant obtained above was mixed with 600 μL of a solution of 0.5 mol/L tri-n-octylamine in chloroform. After extracting TCA in the organic layer, the cAMP content in the water layer sample was measured according to the method described in cAMP assay kit.

The strength of DP receptor antagonistic activity of the compound of the present invention was represented by IC$_{50}$ (concentration of the compound of the present invention required to inhibit by 50% the production of cAMP in the absence of the compound of the present invention) calculated from an inhibition ratio against a cAMP production amount which increases by 3 μmol/L PGD$_2$ stimulation.

IC$_{50}$ values were measured for
(3-((2,6-dimethyl-4-(((2S)-4-methyl-3,4-dihydro-2H-1,4-benzoxazin-2-yl)methoxy)benzoyl)amino)phenyl) acetic acid (abbr. to Comparative compound 1 hereinafter) which is a compound described in Example 13 (10) of WO 2005/028455(Patent Document 1),
(3-((2,6-dimethyl-4-(((2S)-4-methyl-3,4-dihydro-2H-1,4-benzoxazin-2-yl)methoxy)benzoyl)amino) -4-methylphenyl)acetic acid (abbr. to Comparative compound 2 hereinafter) which is a compound described in Example 13 (19) of Patent Document 1,
(4-chloro-3-((2,6-dimethyl-4-(((2S)-4-methyl-3,4-dihydro-2H-1,4-benzoxazin-2-yl)methoxy)benzoyl)amino)phenyl)acetic acid (abbr. to Comparative compound 3 hereinafter) which is a compound described in Example 13 (2) of Patent Document 1, and
1-(4-chloro-3-((2,6-dimethyl-4-(((2S)-4-methyl-3,4-dihydro-2H-1,4-benzoxazin-2-yl)methoxy)benzoyl)amino)

phenyl)cyclopropanecarboxylic acid (abbr. to Comparative compound 4 hereinafter) which is a compound described in Example 38 of Patent Document 1, by the method described above, and it was found that $IC_{50}$ values for Comparative compounds 1, 3, and 4 were 0.021 µmol/L, 0.004 µmol/L, and 0.0065 µmol/L, respectively.

Thus, it was found that the compound represented by the above-mentioned formula (A) which has a methyl group (Comparative compound 2) or a chloro group (Comparative compound 4) at 4-position of the phenylacetic acid moiety thereof has more increased binding activity against the DP receptor than the non-substituted compound (Comparative compound 1).

On the other hand, it was found that the compound of the present invention represented by formula (I) has a pharmaceutically significant antagonistic activity against the DP receptor. For example, $IC_{50}$ values of the compounds described in Examples 12, 21, and 24 are 0.0071 µmol/L, 0.0029 µmol/L, and 0.0089 µmol/L, respectively.

Biological Example 2

Measurement of Drug-Metabolizing Enzyme Inhibitory Activity (human CYP3A4 Inhibitory Effect)

Experimental Method

A solution of the test compound having a concentration five hundred times more than the evaluation concentration in ethanol, or ethanol was 125-fold diluted by water. 50 µL of the test compound solution or the ethanol solution (control) was added with CYP3A4 substrate (7-benzyloxyquinoline (7-BQ), 40 µmol/L), magnesium chloride solution (5 mmol/L), and 100 µL of 200 mM potassium phosphate buffer solution (pH 7.4) containing CYP3A4 expression system microsome (BD Gentest, 0.25 mg/mL), and preincubated at 37° C. for 10 minutes, then added with 50 µL of reduced nicotinamide adenine dinucleotide phosphate (NADPH, final concentration 1 mmol/L) and incubated at 37° C. for 30 minutes. Immediately after the addition of NADPH, and after incubation, the fluorescence intensity was measured for 7-hydroxyquinoline which is a metabolite of the substrate (excitation wavelength 409 nm, emission wavelength 530 nm). The inhibition ratio against the control was calculated by the equation below.

Inhibition rate (%)=[1-{(fluorescence intensity of the test compound after incubation—fluorescence intensity of the test compound immediately after addition of NADPH)/(fluorescence intensity of control after incubation—fluorescence intensity of control immediately after the addition of NADPH))]}×100.

$IC_{50}$ was calculated from the equation below.

$IC_{50}$ (µmol/L)=(50−(D×A−C×B)/(D−C)/((B−A)/(D−C))

A: Highest inhibition rate (%) which is less than 50%.
B: Lowest inhibition rate (%) which is more than 50%.
C: Concentration (µmol/L) of the test compound when the inhibition rate is A.
D: Concentration (µmol/L) of the test compound when the inhibition rate is B.

$IC_{50}$ values measured for Comparative compounds 1, 2, 3, and 4 by the above-mentioned method were 30 µmol/L or more, less than 3 µmol/L, 19.7 µmol/L, and 30 µmol/L or more, respectively.

That is, it was found that the compound represented by above-mentioned formula (A) having a methyl group introduced, at 4-position of the phenylacetic acid moiety (Comparative compound 2) has a remarkably strong inhibition performance against CYP3A4, which is a drug-metabolizing enzyme, compared to the non-substituted compound. It was also found that when a chloro group is introduced at 4-position of the phenylacetic acid moiety of the compound represented by the above-mentioned formula (A), CYP3A4 is not affected by the compound.

Measurement of inhibitory activity of the compound of the present invention represented, by formula (I) by the above-mentioned measuring method revealed that the inhibitory activity thereof against CYP3A4 is not strong. For example, $IC_{50}$ values of the compounds described in Example 12, 21, and 24 are 30 µmol/L or more, 30 µmol/L or more, and 8.4 µmol/L, respectively.

Biological Example 3

Receptor Binding Experiment Using Prostanoid Receptor Subtype expressing Cell

According to the method of Sugimoto et. al. (J. Biol. Chem. 267, 6463-6466 (1992)), CHO cells in which prostanoid receptor subtype (human $EP_2$) was expressed were prepared to obtain membrane preparation.

A reaction solution (200 µl) containing membrane fraction preparation (0.5 mg/ml) and $^3H$-$PGE_2$ was incubated at room temperature for one hour. The reaction was terminated by ice-cooled buffer (3 ml), bound $^3H$-$PGE_2$ was trapped on a glass filter (GF/B) by suction filtration at reduced pressure, and bound radioactivity was measured by a liquid scintillator.

The Kd value was calculated from Scatchard plots [Ann. N.Y. Acad. Sci. 51, 660 (1949)]. Nonspecific binding was determined as a bond in the presence of excessive amount (10 µM) of unlabeled $PGE_2$. The measurement of $^3H$-$PGE_2$ binding inhibitory effect by the compound of the present invention was carried out by adding $^3H$-$PGE_2$ (2.5 nM) and the compound of the present invention at a variety of concentrations. Note that all reactions used the following buffer.

Buffer: potassium phosphate (10 mM, pH 6.0), EDTA (1 mM), $MgCl_2$ (10 mM), NaCl (0.1 M).

Dissociation constant (Ki (µM)) of each compound was calculated from the following equation.

$Ki=IC_{50}/(1+([C]/Kd)$ $IC_{50}$: Concentration of the compound of the present invention required for 50%-inhibition of [3H]$PGE_2$ specific bond
C: Concentration of [3H]$PGE_2$
Kd: Dissociation constant of [3H]$PGE_2$ Ki values of Comparative compounds 1, 3, and 4 measured by the above-mentioned method were 0.0936 µmol/L, 0.0168 µmol/L and 0.0018 µmol/L, respectively.

That is, it was found that when a compound represented by the above-mentioned formula (A) has a hydrogen atom or a chloro group at 4-position of the phenylacetic acid moiety, its binding affinity to the $EP_2$ receptors is very strong.

On the other hand, it was found that the compound represented by formula (I) does not have strong binding affinity to the $EP_2$ receptors. For example, the Ki value of the compound described in Example 12 is 0.142 µmol/L.

The compounds described in Example 12 are the compounds represented by formula (A) in Patent Document 1 in which $R^{2A}$ represents a trifluoromethyl group and is substituted at the 4-position of the phenylacetic acid part, and $R^{12A}$ and $R^{13A}$ taken together represent an optionally oxidized C2-5 alkylene group.

Comparative compound 4 is a compound represented by formula (A) in Patent Document 1 in which $R^{2A}$ represents a chlorine atom and is substituted at 4-position of the phenylacetic acid moiety, and $R^{12A}$ and $R^{13A}$ taken together represent an optionally oxidized C2-5 alkylene group.

That is, the above-mentioned results show that among the compounds represented by formula (A), only the compounds in which $R^{2A}$ represents trifluoromethyl group and is substituted at 4-position of the phenylacetic acid moiety, and $R^{12A}$ and $R^{13A}$ taken together represent an optionally C2-5 alkylene group, can be dissociated from binding activity against $EP_2$ receptors.

Formulation Example 1

The following components were mixed by a conventional method and were punched out to obtain 10,000 tablets each containing 10 mg of the active ingredient.

| | |
|---|---|
| 1-(3-((2,6-dimethyl-4-(((2S)-4-methyl-3,4-dihydro-2H-1,4-benzoxazin-2-yl)methoxy)benzoyl)amino)-4-(trifluoromethyl)phenyl)cyclopropanecarboxylic acid | 100 g |
| Carboxymethyl Cellulose calcium (Disintegrator) | 20 g |
| Magnesium stearate (Lubricant) | 10 g |
| Microcrystalline cellulose | 870 g |

Formulation Example 2

After the following components were mixed by a conventional method, the mixture was filtered with a dust-removal-filter and was filled in 5 ml portions into ampoules. The ampoules were heat-sterilized by autoclave to obtain 10,000 ampoules each containing 20 mg of an active ingredient.

| | |
|---|---|
| 1-(3-((2,6-dimethyl-4-(((2S)-4-methyl-3,4-dihydro-2H-1,4-benzoxazin-2-yl)methoxy)benzoyl)amino)-4-(trifluoromethyl)phenyl)cyclopropanecarboxylic acid | 200 g |
| Mannitol | 20 g |
| Distilled water | 50 L |

[Industrial Applicability]

Since the compounds of the present invention represented by formula (I) bind and antagonize to DP receptors, it is considered that the compounds are useful for the prevention and/or treatment of diseases mediated by DP receptors such as allergic disease, systemic mastocytosis, disorders accompanied by systemic mast cell activation, anaphylaxis shock, bronchoconstriction, urticaria, eczema, pimples, allergic bronchial pulmonary aspergillosis, sinusitis, migraine, nasal polypus, anaphylactic vasculitis, eosinophilic syndrome, contact dermatitis, diseases accompanied by itch, diseases which are generated secondarily as a result of behavior accompanied by itch, inflammation, chronic obstructive pulmonary diseases, ischemic reperfusion injury, cerebrovascular accident, autoimmune disease, traumatic brain disorder, hepatopathy, graft rejection, rheumatoid arthritis, pleurisy, osteoarthritis, Crohn's disease, ulcerative colitis, irritable bowel syndrome, interstitial cystitis, muscular dystrophy, polymyositis, cancer, leukemia, viral infection, or multiple sclerosis. Further the compounds are considered to relate to sleeping and platelet aggregation and to be useful against the relevant diseases. In addition, since the inhibitory effect of the compounds of the present invention represented by formula (I) against a drug-metabolizing enzyme is not strong and the compounds have good selectivity to the DP receptors, the compounds can be used as a safe drug.

The invention claimed is:

1. A method for making a compound of the formula (IA):

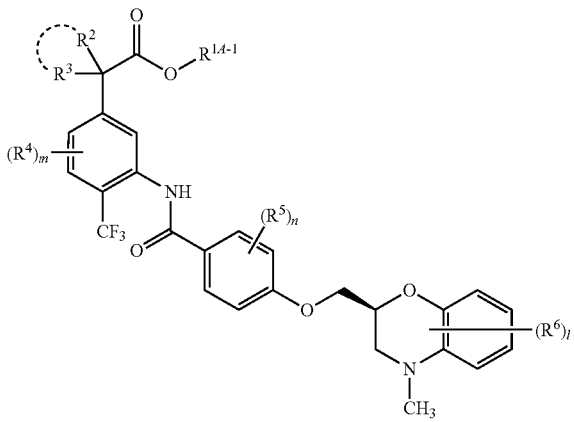

(IA)

wherein $R^{14-1}$ represents a $C_{1-4}$ alkyl group, $R^2$ and $R^3$ taken together represent a $C_{2-5}$ alkylene group, $R^4$, $R^5$ and $R^6$ each independently represents a halogen atom, optionally oxidized $C_{1-6}$ alkyl group, optionally protected hydroxyl group, trihalomethyl group, —$SO_2R^7$ group, —$SOR^7$ group or —$SR^7$ group, $R^7$ represents a $C_{1-6}$ alkyl group or a phenyl, tolyl or xylyl group, indicates that the bond is attached in front of the sheet, m represents 0 or an integer from 1 to 3, n represents 0 or an integer from 1 to 4, and i represents 0 or an integer from 1 to 7, with the proviso that when m is 2 or more, each $R^4$ may be the same or different selected from the above-defined groups, when n is 2 or more, each $R^5$ may be the same or different selected from the above-defined groups, and when i is 2 or more, each $R^6$ may be the same or different selected from the above-defined groups, which comprises:

subjecting a compound of formula (II):

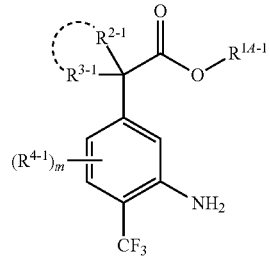

(II)

wherein $R^{2-1}$, $R^{3-1}$, and $R^{4-1}$ respectively have the same meanings as $R^2$, $R^3$, and $R^4$, and other symbols have the meaning above, and a compound of formula (III):

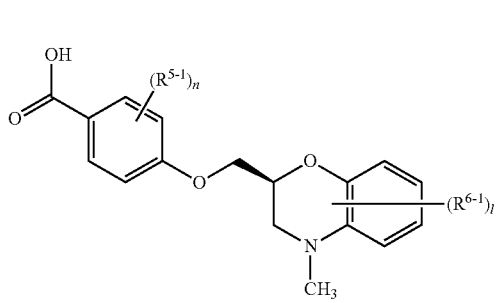

wherein $R^{5-1}$ and $R^{6-1}$ respectively have the same meanings as $R^5$ and $R^6$, and other symbols have the same meanings as above, to an amidation reaction, optionally followed by a deprotection reaction.

2. A method for making a compound of the formula (IB):

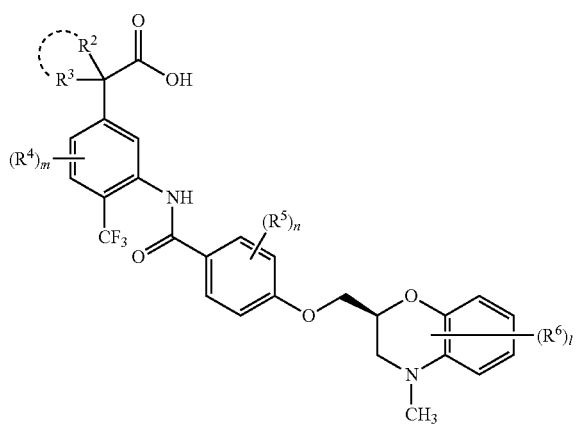

wherein $R^2$ and $R^3$ taken together represent a $C_{2-5}$ alkylene group, $R^4$, $R^5$ and $R^6$ each independently represents a halogen atom, optionally oxidized $C_{1-6}$ alkyl group, optionally protected hydroxyl group, trihalomethyl group, —$SO_2R^7$ group, —$SOR^7$ group or —$SR^7$ group, $R^7$ represents a $C_{1-6}$ alkyl group or a phenyl, tolyl or xylyl group, ▲ indicates that the bond is attached in front of the sheet, m represents 0 or an integer from 1 to 3, n represents 0 or an integer from 1 to 4, and i represents 0 or an integer from 1 to 7, with the proviso that when m is 2 or more, each $R^4$ may be the same or different selected from the above-defined groups, when n is 2 or more, each $R^5$ may be the same or different selected from the above-defined groups, and when i is 2 or more, each $R^6$ may be the same or different selected from the above-defined groups, which comprises:

subjecting a compound of the formula (IA):

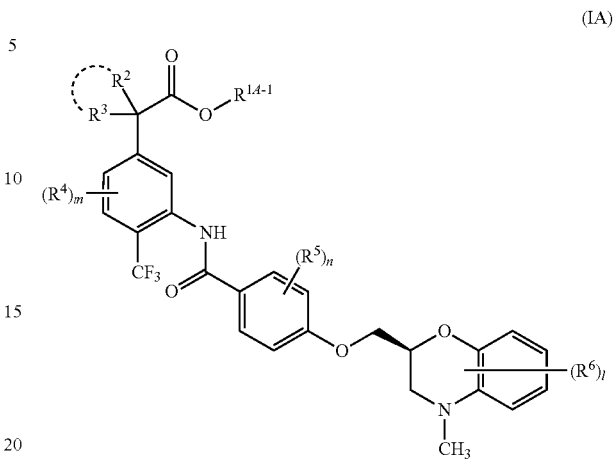

wherein $R^{14-1}$ represents a $C_{1-4}$ alkyl group and other symbols have the same meanings as above, to a deprotection reaction to remove $R^{14-1}$ from the carboxyl group, optionally followed by a deprotection reaction to remove a protective group on any hydroxyl group.

3. A method for the treatment of allergic disease comprising administering an effective dose of a compound of the formula (I-a):

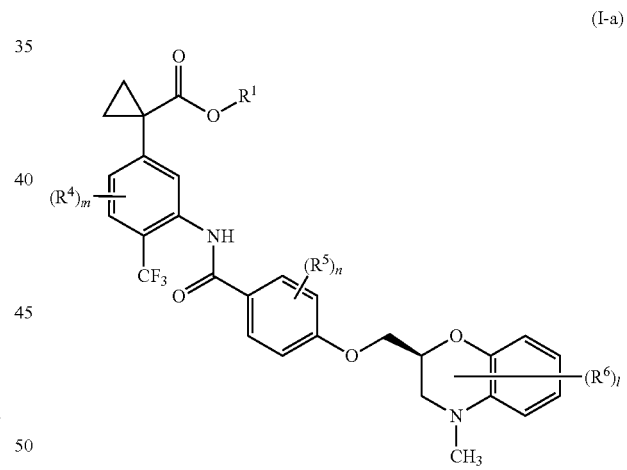

wherein $R^1$ represents a hydrogen atom or a $C_{1-4}$ alkyl group, $R^4$, $R^5$ and $R^6$ each independently represents a halogen atom, optionally oxidized $C_{1-6}$ alkyl group, optionally protected hydroxyl group, trihalomethyl group, —$SO_2R^7$ group, —$SOR^7$ group or —$SR^7$ group, $R^7$ represents a $C_{1-6}$ alkyl group or a phenyl, tolyl or xylyl group, ▲ indicates that the bond is attached in front of the sheet, m represents 0 or an integer from 1 to 3, n represents 0 or an integer from 1 to 4, and i represents 0 or an integer from 1 to 7, with the proviso that when m is 2 or more, each $R^4$ may be the same or different selected from the above-defined groups, when n is 2 or more, each $R^5$ may be the same or different selected from the above-defined groups, and when i is 2 or more, each $R^6$ may be the same or different selected from the above-defined groups, or a salt thereof, an N-oxide thereof or a solvate thereof, or a prodrug thereof, to an allergic patient in combination with an antihistaminic agent.

4. A method for the treatment of allergic disease comprising administering an effective dose of a compound selected from the group consisting of:

(1) 1-(3-((2-ethyl-4-(((2S)-4-methyl-3,4-dihydro-2H-1,4-benzoxazin-2-yl)methoxy)benzoyl)amino)-4-(trifluoromethy)phenyl)cyclopropanecarboxylic acid, (2) 1-(3-((2-ethyl-6-methyl-4-(((2S)-4-methyl-3,4-dihydro-2H-1,4-benzoxazin-2-yl)methoxy)benzoyl)amino)-4-(trifluoromethyl)phenyl)cyclopropanecarboxylic acid, (3) (3-((2,6-dimethyl-4-(((2S)-4-methyl-3,4-dihydro-2H-1,4-benzoxazin-2-yl)methoxy)benzoyl)amino)-4-(trifluoromethyl)phenyl)acetic acid, (4) (3-((2-ethyl-6-methyl-4-(((2S)-4-methyl-3,4-dihydro-2H-1,4-benzoxazin-2-yl)methoxy)benzoyl)amino)-4-(trifluoromethyl)phenyl)acetic acid, (5) hydroxy(3-((2,6-dimethyl-4-(((2S)-4-methyl-3,4-dihydro-2H-1,4-benzoxazin-2-yl)methoxy)benzoyl)amino)-4-(trifluoromethy)phenyl)acetic acid, and (6) 2-hydroxy-2-(3-((2,6-dimethyl-4-(((2S)-4-methyl-3,4-dihydro-2H-1,4-benzoxazin-2-yl)methoxy)benzoyl)amino)-4-(trifluoromethyl)phenyl)propionic acid, and (7) 1-(3-((2,6-dimethyl-4-(((2S)-4-methyl-3,4-dihydro-2H-1,4-benzoxazin-2-yl)methoxy)benzoyl)amino)-4-(trifluoromethyl)phenyl)cyclopropanecarboxylic acid hydrate or a salt thereof, an N-oxide thereof or a solvate thereof, or a prodrug thereof, to an allergic patient in combination with an antihistaminic agent.

5. The method of claim 3, wherein the allergic disease is allergic rhinitis, allergic conjunctivitis, atopic dermatitis, bronchial asthma or food allergy.

6. The method of claim 4, wherein the allergic disease is allergic rhinitis, allergic conjunctivitis, atopic dermatitis, bronchial asthma or food allergy.

7. A pharmaceutical composition comprising 1-(3-((2,6-dimethyl-4-(((2S)-4-methyl-3,4-dihydro-2H-1,4-benzoxazin-2-yl)methoxy)benzoyl)amino)-4-(trifluoromethyl)phenyl)cyclopropanecarboxylic acid, or a salt thereof, an N-oxide thereof or a hydrate thereof, as an active ingredient.

8. The pharmaceutical composition of claim 7, further comprising one or more other compounds selected from the group consisting of an antihistaminic agent, suppressor for mediator liberation, thromboxane synthetase inhibitor, antagonist for thromboxane A2 receptor, antagonist for leukotriene receptor, leukotriene synthase inhibitor, cytokine inhibitor, steroid agent, sympathomimetic agent, phosphodiesterase IV inhibitor, xanthine derivative, anticholinergic agent, anti-IgE antibody formulation, immunosuppressive agent, chemokine receptor antagonist, adhesion molecule inhibitor, other prostanoid receptor antagonist, nonsteroidal anti-inflammatory agent, and a nitric oxide synthase inhibitor.

* * * * *

UNITED STATES PATENT AND TRADEMARK OFFICE
CERTIFICATE OF CORRECTION

| | | |
|---|---|---|
| PATENT NO. | : 8,809,524 B2 | Page 1 of 1 |
| APPLICATION NO. | : 13/854329 | |
| DATED | : August 19, 2014 | |
| INVENTOR(S) | : Naganawa et al. | |

It is certified that error appears in the above-identified patent and that said Letters Patent is hereby corrected as shown below:

In the Claims

Column 47, line 28 claim 4 reads "(trifluoromethy)phenyl)acetic acid, and" should read
-- (trifluoromethyl)phenyl)acetic acid, and --

Signed and Sealed this
Twenty-fourth Day of March, 2015

Michelle K. Lee
*Director of the United States Patent and Trademark Office*